(12) United States Patent
Grabber et al.

(10) Patent No.: US 8,685,672 B2
(45) Date of Patent: Apr. 1, 2014

(54) INCORPORATION OF FLAVAN-3-OLS AND GALLIC ACID DERIVATIVES INTO LIGNIN TO IMPROVE BIOMASS UTILIZATION

(75) Inventors: John H. Grabber, Mazomanie, WI (US); John Ralph, Madison, WI (US)

(73) Assignees: Wisconsin Alumni Research Foundation, Madison, WI (US); The United States of America as Represented by the Secretary of Agriculture, Washington, DC (US)

( * ) Notice: Subject to any disclaimer, the term of this patent is extended or adjusted under 35 U.S.C. 154(b) by 167 days.

(21) Appl. No.: 13/090,206

(22) Filed: Apr. 19, 2011

(65) Prior Publication Data

US 2012/0094330 A1 Apr. 19, 2012

Related U.S. Application Data

(60) Provisional application No. 61/325,695, filed on Apr. 19, 2010.

(51) Int. Cl.
- *C12P 19/00* (2006.01)
- *C12N 1/00* (2006.01)
- *C08H 7/00* (2011.01)

(52) U.S. Cl.
USPC .......................... 435/72; 435/317.1; 530/500

(58) Field of Classification Search
USPC .................. 435/72, 317.1; 530/500
See application file for complete search history.

(56) References Cited

U.S. PATENT DOCUMENTS

2004/0261198 A1* 12/2004 Kainz et al. ................ 8/405

OTHER PUBLICATIONS

Gizdavic-Nikolaidis et al., Conducting polymers as free radical scavengers, 2004, Synthetic Metals, 140, 225-232.*
Arrieta-Baez, D.; Stark, R.E.; Modeling suberization with peroxidase-catalyzed polymerization of hydroxycinnamic acids: Cross-coupling and dimerization reactions. *Phytochemistry* (2006), 67:743-753.
Blee, K.A.; Wheatley, E.R.; Bonham, V.A.; Mitchell, G.P.; Robertson, D.; Slabas, A.R.; Burrell, M.M.; Wojtaszek, P.; Bolwell, G.P., Proteomic analysis reveals a novel set of cell wall proteins in a transformed tobacco cell culture that synthesises secondary walls as determined by biochemical and morphological parameters. *Planta* (2001), 212(3), 404-415.
Boerjan, W.; Ralph, J.; Baucher, M., Lignin Biosynthesis. *Annu. Rev. Plant Biol.* (2003), 54, 519-549.
Bunzel, M.; Ralph J.; Funk, C.; Steinhart, H., Isolation and identification of a ferulic acid dehydrotrimer from saponified maize bran insoluble fiber. *Eur Food Res Technol* (2003), 217:128-133.
Buxton, D.R.; Brasche, M.R., Digestibility of structural carbohydrates in cool-season grass and legume forages. *Crop Science* (1991), 31:1338-1345.

Chapple, C.; Ladisch, M.; Meilan, R., Loosening lignin's grip on biofuel production. *Nature Biotechnol.* (2007), 25(7), 746-748.
Chen, F.; Dixon, R.A., Lignin modification improves fermentable sugar yields for biofuel production. *Nature Biotechnol.* (2007), 25(7), 759-761.
Clifford, M.N., Chlorogenic acids and other cinnamates—nature, occurrence and dietary burden. *J Sci Food Agric* (1999), 79:362-372.
Doane, P.H; Schofield, P.; Pell, A.N., Neutral detergent fiber disappearance and gas, and volatile fatty acid production during the in vitro fermentation of six forages. *J Anim Sci* (1997), 75:3342-3352.
Dubois, M.; Giles, K.A.; Hamilton, J.K.; Rebers, P.A.; Smith, F., Colorimetric method for determination of sugars and related substances. *Anal Chem* (1956), 28:350-356.
Evans, J.J.; Himmelsbach, D.S., Incorporation of peroxidase into synthetic lignin. *J Agric Food Chem* (1991), 39:830-832.
Ferrer, M.A.; Barcelo, A.R., Inactivation of cell wall acidic peroxidase isoenzymes during the oxidation of coniferyl alcohol in Lupinus. *Phytochemistry* (1994), 36:1161-1163.
Franke, R.; Hemm, M.R.; Denault, J.W.; Ruegger, M.O.; Humphreys, J.M.; Chapple, C., Changes in secondary metabolism and deposition of an unusual lignin in the *ref8* mutant of *Arabidopsis*. *Plant J.* (2002), 30(1), 47-59.
Getachew, G; Blummel, M.; Makkar H.P.S.; Becker K.; In vitro gas measuring techniques for assessment of nutritional quality of feeds: a review. *Anim Feed Sci Technol* (1998), 72:261-281.
Grabber, J.H.; Hatfield, R.D.; Ralph J.; Zon, J.; Amrhein, N., Ferulate cross-linking in cell walls isolated from maize cell suspensions. *Phytochemistry* (1995), 40:1077-1082.
Grabber, J.H.; Ralph, J.; Hatfield, R.D.; Quideau, S.; Kuster, T.; Pell, A.N., Dehydrogenation polymer-cell wall complexes as a model for lignified grass walls. *J. Agr. Food Chem.* (1996), 44(6), 1453-1459.

(Continued)

*Primary Examiner* — Kristin Vajda

(74) *Attorney, Agent, or Firm* — Joseph T. Leone, Esq.; Daniel A. Blasiole; DeWitt Ross & Stevens S.C.

(57) ABSTRACT

A method of manufacturing modified lignin and the resulting non-natural modified lignin product in which a lignin-producing polymerization reaction is performed using a polymerizable monomer having the structure:

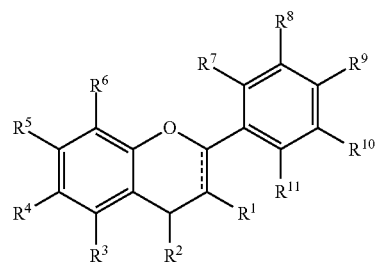

wherein at least one of the polymerizable monomers is incorporated into the resulting lignin.

19 Claims, 12 Drawing Sheets

(56) References Cited

OTHER PUBLICATIONS

Grabber, J.H.; Hatfield, R.D.; Ralph, J., Diferulate cross-links impede the enzymatic degradation of nonlignified maize walls. *J. Sci. Food Agr.* (1998), 77(2), 193-200.

Grabber, J.H.; Ralph, J; Hatfield, R.D.; Cross-Linking of maize walls by ferulate dimerization and incorporation into lignin. *J Agric Food Chem* (2000), 48:6106-6113.

Grabber, J.H.; Hatfield, R.D.; Ralph, J., Apoplastic pH and monolignol addition rate effects on lignin formation and cell wall degradability in maize. *J Ag Food Chem* (2003), 51:4984-4989.

Grabber, J.H.; Hatfield, R.D., Methyl esterification divergently affects the degradability of pectic uronosyls in nonlignified and lignified maize cell walls. *J Ag Food Chem* (2005), 53:1546-1549.

Grabber, J.H., How do lignin composition, structure, and cross-linking affect degradability? A review of cell wall model studies. *Crop Sci* (2005), 45:820-831.

Grabber J.H.; Lu, F., Formation of syringyl-rich lignins in maize as influenced by feruloylated xylans and p-coumaroylated monolignols. *Planta* (2007), 226:741-751.

Grabber, J.H.; Hatfield, R.D.; Lu, F.; Ralph, J., Coniferyl ferulate incorporation into lignin enhances the alkaline delignification and enzymatic degradation of cell walls. *Biomacromolecules* (2008), 9:2510-2516.

Grabber, J.H.; Mertens, D.R.; Kim, H.; Funk, C.; Lu, F.; Ralph, J., Cell wall fermentation kinetics are impacted more by lignin content and ferulate cross-linking than by lignin composition. *J Sci Food Agric* (2009), 89:122-129.

Guyot, S.; Vercauteren, J.; Cheynier, V., Structural determination of colourless and yellow dimers resulting from (+)-catechin coupling catalysed by grape polyphenoloxidase. *Phytochemistry* (1996), 42:1279-1288.

Hatfield, R.D.; Jung, H.G.; Ralph, J.; Buxton, D.R.; Weimer, P.J., A comparison of the insoluble residues produced by the Klason lignin and acid detergent lignin procedures. *J Sci Food Agric* (1994), 65:51-58.

Hatfield, R.D.; Ralph, J.; Grabber, J.H., A potential role for sinapyl p-coumarate as a radical transfer mechanism in grass lignin formation. *Planta* (2008), 228:919-928.

M. Hedenström, S. Wiklund-Lindstrom, T. Öman, F. Lu, L. Gerbner, P. F. Schatz, B. Sundberg and J. Ralph. Identification of Lignin and Polysaccharide Modifications in Populus Wood by Chemometric Analysis of 2D NMR Spectra from Dissolved Cell Walls. *Molecular Plant*, (2009), 2, 933-942.

Hemmerle, H.; Burger, H.J.; Below, P.; Schubert, G.; Rippel, R.; Schindler, P.W.; Paulus, E.; Herling, A.W., Chlorogenic acid and synthetic chlorogenic acid derivatives: Novel inhibitors of hepatic glucose-6-phosphate translocase. *J Med Chem* (1997), 40:137-145.

Holtzapple, M.T.; Lundeen, J.E.; Sturgis, R.; Lewis, J.E.; Dale, B.E., Pretreatment of lignocellulosic municipal solid waste by ammonia fiber explosion (AFEX). *Appl. Biochem. Biotechnol* (1992), 0273-2289.

Hosny, M.; Rosazza, J.P.N., Novel oxidations of (+)-catechin by horseradish peroxidase and laccase. *J Ag Food Chem* (2002), 50:5539-5545.

Huang, L.S.; Colas, C.; De Montellano, P.R.O., Oxidation of carboxylic acids by horseradish peroxidase results in prosthetic heme modification and inactivation. *J. Am. Chem. Soc.* (2004), 126(40), 12865-12873.

Huang, Q.; Huang, Q.; Pinto, R.A.; Griebenow, K.; Schweitzer-Stenner, R.; Weber, Jr W.J., Inactivation of horseradish peroxidase by phenoxyl radical attack. *J Am Chem Soc* (2005), 127:1431-1437.

Kim, H.; Ralph, J., Simplified preparation of coniferyl and sinapyl alcohols. *J Ag Food Chem* (2005), 55:3693-3695.

Kim, H.; Ralph, J.; Akiyama, T., Solution-state 2D NMR of ball-milled plant cell wall gels in DMSO-d6. *Bioenerg Res* (2008), 1:56-66.

Kim, H.; Ralph, J., Solution-state 2D NMR of ball-milled plant cell wall gels in DMSOd6/pyridine-d5. *Org Biomol Chem* (2010), 8:576-591.

Kusano, R.; Tanaka, T.; Matsuo, Y.; Kouno, I., Structures of epicatechin gallate trimer and tetramer produced by enzymatic oxidation. *Chem Pharm Bull* (2007), 55:1768-1772.

Lopez, S.; Murison, S.D.; Travis, A.J.; Chesson, A.; Degradability of parenchyma and sclerenchyma cell walls isolated at different developmental stages from a newly extended maize internode. *Acta Bot Neerl* (1993), 42:165-174.

Lu, F.; Ralph, J., Derivatization followed by reductive cleavage (DFRC method), a new method for lignin analysis: protocol for analysis of DFRC monomers. *J. Agr. Food Chem.* (1997), 45(7), 2590-2592.

Lu, F.; Ralph, J., Facile synthesis of 4-hydroxycinnamyl p-coumarates. *J Agric Food Chem* (1998), 46:2911-2913.

Lu, F.; Ralph, J., Preliminary evidence for sinapyl acetate as a lignin monomer in kenaf. *Chem. Commun.* (2002), (1), 90-91.

Lu, F.; Ralph, J., Non-degradative dissolution and acetylation of ball-milled plant cell walls; high-resolution solution-state NMR. *Plant J.* (2003), 35(4), 535-544.

Lu, F.; Ralph, J., Novel β-β-structures in natural lignins incorporating acylated monolignols, *Thirteenth International Symposium on Wood, Fiber, and Pulping Chemistry*, Auckland, New Zealand, (2005); APPITA, Australia: pp. 233-237.

Lu, F.; Ralph, J., Novel tetrahydrofuran structures derived from β-β-coupling reactions involving sinapyl acetate in kenaf lignins. *Org Biomol Chem* (2008), 6:3681-3694.

Marita, J.; Ralph, J.; Hatfield, R.D.; Chapple, C., NMR characterization of lignins in *Arabidopsis* altered in the activity of ferulate-5-hydroxylase. *Proc. Natl. Acad. Sci.* (1999), 96(22), 12328-12332.

Ohlsson, A.B.; Djerbi, S.; Winzell, A.; Bessueille, L.; Staldal, V.; Li, X.G.; Blomqvist, K.; Bulone, V.; Teeri, T.T.; Berglund, T., Cell suspension cultures of *Populus tremula* x P-tremuloides exhibit a high level of cellulose synthase gene expression that coincides with increased in vitro cellulose synthase activity. *Protoplasma* (2006), 228(4), 221-229.

Oosterveld, A.; Grabber, J.H.; Beldman, G.; Ralph, J.; Voragen, A.G.J., Formation of ferulic acid dehydrodimers through oxidative cross-linking of sugar beet pectin. *Carbohydr Res* (1997), 300:179-181.

Pan, X.J.; Arato, C.; Gilkes, N.; Gregg, D.; Mabee, W.; Pye, K.; Xiao, Z.Z.; Zhang, X.; Saddler, J., Biorefining of softwoods using ethanol organosolv pulping: Preliminary evaluation of process streams for manufacture of fuel-grade ethanol and coproducts. *Biotechnol. Bioeng.* (2005), 90(4), 473-481.

Quideau, S.; Ralph, J., Facile large-scale synthesis of coniferyl, sinapyl, and p-coumaryl alcohol. *J Agric Food Chem* (1992), 40:1108-1110.

Ralph, J.; Helm, R.F.; Quideau, S.; Hatfield, R.D., Lignin-feruloyl ester cross-links in grasses. Part 1. Incorporation of feruloyl esters into coniferyl alcohol dehydrogenation polymers. *J. Chem. Soc., Perkin Trans. 1* (1992), (21), 2961-2969.

Ralph, J.; Mackay, J.J.; Hatfield, R.D.; O'Malley, D.M.; Whetten, R.W.; Sederoff, R.R., Abnormal lignin in a loblolly pine mutant. *Science* (1997), 277, 235-239.

Ralph, J.; Hatfield, R.D.; Piquemal, J.; Yahiaoui, N.; Pean, M.; Lapierre, C.; Boudet, A.-M., NMR characterization of altered lignins extracted from tobacco plants down-regulated for lignification enzymes cinnamyl-alcohol dehydrogenase and cinnamoyl-CoA reductase. *Proc. Natl. Acad. Sci.* (1998), 95(22), 12803-12808.

Ralph, J.; Kim, H.; Peng, J.; Lu, F., Arylpropane-1,3-diols in lignins from normal and CAD-deficient pines. *Org. Lett.* (1999), 1(2), 323-326.

Ralph, J.; Lapierre, C.; Marita, J.; Kim, H.; Lu, F.; Hatfield, R.D.; Ralph, S.A.; Chapple, C.; Franke, R.; Hemm, M.R.; Van Doorsselaere, J.; Sederoff, R.R.; O'Malley, D.M.; Scott, J.T.; Mackay, J.J.; Yahiaoui, N.; Boudet, A.-M.; Pean, M.; Pilate, G.; Jouanin, L.; Boerjan, W., Elucidation of new structures in lignins of CAD- and COMT-deficient plants by NMR. *Phytochem.* (2001), 57(6), 993-1003.

Ralph, J.; Lundquist, K.; Brunow, G.; Lu, F.; Kim, H.; Schatz, P.F.; Marita, J.M.; Hatfield, R.D.; Ralph, S.A.; Christensen, J.H.; Boerjan, W., Lignins: natural polymers from oxidative coupling of 4-hydroxyphenylpropanoids. *Phytochem. Revs.* (2004),3(1), 29-60.

Ralph, J.; Bunzel, M.; Marita, J.M.; Hatfield, R.D.; Lu, F.; Kim, H.; Schatz, P.F.; Grabber, J.H.; Steinhart, H., Peroxidase-dependent

(56) References Cited

OTHER PUBLICATIONS cross-linking reactions of *p*-hydroxycinnamates in plant cell walls. *Phytochem. Revs.* (2004), 3(1), 79-96.
Ralph, S.A.; Landucci, L.L.; Ralph, J., NMR Database of Lignin and Cell Wall Model Compounds. Available over Internet at http://ars.usda.gov/Services/docs.htm?docid=10429, updated at least annually since 1993. (2005).
Ralph, J., What makes a good monolignol substitute? In *The Science and Lore of the Plant Cell Wall Biosynthesis, Structure and Function*, Hayashi, T., Ed. Universal Publishers (BrownWalker Press): Boca Raton, FL, (2006); pp. 285-293.
Ralph, J.; Akiyama, T.; Kim, H.; Lu, F.; Schatz, P.F.; Marita, J.M.; Ralph, S.A.; Reddy, M.S.S.; Chen, F.; Dixon, R.A., Effects of coumarate-3-hydroxylase downregulation on lignin structure. *J. Biol. Chem.* (2006), 281(13), 8843-8853.
Ralph, J.; Brunow, G.; Boerjan, W., Lignins. In *Encyclopedia of Life Sciences*, John Wiley & Sons, Ltd.: Chichester, UK, (2007); in press.
Ralph, J.; Brunow, G.; Harris, P.J.; Dixon, R.A.; Boerjan, W., Lignification: Are lignins biosynthesized via simple combinatorial chemistry or via proteinaceous control and template replication? In *Advances in Polyphenols Research*, Daayf, F.; El Hadrami, A.; Adam, L.; Ballance, G.M., Eds. Blackwell Publishing: Oxford, UK, (2007); in press.
Ralph, J.; Kim, H.; Lu, F.; Grabber, J.H.; Boerjan, W.; Leplé, J.-C.; Berrio Sierra, J.; Mir Derikvand, M.; Jouanin, L.; Lapierre, C., Identification of the structure and origin of a thioacidolysis marker compound for ferulic acid incorporation into angiosperm lignins (and a *pseudo*-marker compound for cinnamoyl-CoA reductase deficiency). *Plant J.* (2007), submitted.
Ralph, J.; Schatz, P.F.; Lu, F.; Kim, H.; Akiyama, T.; Nelsen, S.F., Quinone methides in lignification. In: *Quinone Methides*. Edited by Rokita S. Hoboken, NJ: Wiley-Blackwell; (2009).
Russell, W.R.; Burkitt, M.J.; Scobbie, L.; Chesson, A., Radical formation and coupling of hydroxycinnamic acids containing 1,2-dihydroxy substituents. *Bioorganic Chem* (2003), 31:206-215.
Steel, R.G.D.; Torrie, J.H., Principles and procedures of statistics, 2nd edition. New York: McGraw-Hill Publishing Co.; (1980).
Stewart, J.J.; Akiyama, T.; Chapple, C.C.S.; Ralph, J.; Mansfield, S.D., Lignins with Extreme Syringyl Levels: The Effects of Over-Expression of Ferulate 5-Hydroxylase on Lignin Structure in Hybrid Poplar. *J. Biol. Chem.* (2007), submitted.

Tobimatsu, Y.; Takano, T.; Kamitakahara, H.; Nakatsubo, F., Studies on the dehydrogenative polymerizations of monolignol beta-glycosides. Part 2: Horseradish peroxidase catalyzed dehydrogenative polymerization of isoconiferin. *Holzforschung* (2006), 60(5), 513-518.
Ulibarri, G.; Nadler, W.; Skrydstrup, T.; Audrain, H.; Chiaroni, A.; Riche, C.; Grierson, D.S., Construction of the bicyclic core structure of the enediyne antibiotic Esperamicin-a(1) in either enantiomeric form from (-)-quinic acid. *J Org Chem* (1995), 60:2753-2761.
Van Soest, P.J.; Van Amburgh, M.E.; Robertson, J.B.; Knaus, W.F.; Validation of the 2.4 times lignin factor for ultimate extent of NDF digestion, and curve peeling rate of fermentation curves into pools. In: *Cornell Nutrition Conference for Feed Manufacturers*; Syracuse, New York: Cornell University, Ithaca, New York; (2005): 139-149.
Vanholme, R.; Morreel, K.; Ralph, J.; Boerjan, W., Lignin engineering. *Curr Opin Plant Biol* (2008), 11:1-8.
Wagner, A.; Ralph, J.; Akiyama, T.; Flint, H.; Phillips, L.; Torr, K.M.; Nanayakkara, B.; TE Kiri, L., Modifying lignin in conifers: The role of HCT during tracheary element formation in *Pinus radiata* Proc. Natl. Acad. Sci. (2007), 104(28), 11856-11861.
Ward, G.; Hadar, Y.; Dosoretz, C.G., Inactivation of lignin peroxidase during oxidation of the highly reactive substrate ferulic acid. *Enzyme Microb Tech* (2001), 29(1), 34-41.
Weimer, P.J.; Mertens, D.R.; Ponnampalam, E.; Severin, B.F.; Dale, B.E., Fibex-treated rice straw as a feed ingredient for lactating dairy cows. *Anim Feed Sci Technol* (2003), 103:41-50.
Weimer, P.J.; Dien, .BS.; Springer, T.L.; Vogel, K.P., In vitro gas production as a surrogate measure of the fermentability of cellulosic biomass to ethanol. *Appl Microbiol Biotechnol* (2005), 67:52-58.
Yelle, D.L.; Ralph, J. and Frihart, C.R.; Characterization of non-derivatized plant cell walls using high-resolution solution-state NMR spectroscopy, *Magnetic Resonance in Chemistry*, (2008), 46:508-517.
Zhu, N.; Huang, T.C.; Yu, Y.; Lavoie, E.J.; Yang, C.S.; Ho, C.T., Identification of oxidation products of (-)-epigallocatechin gallate and (-)-epigallocatechin with $H_2O_2$. *J Ag Food Chem* (2000), 48:979-981.
Zhu, N.; Wang, M.; Wei, G.J.; Lin, J.K.; Yang, C.S.; Ho, C.T., Identification of reaction products of (-)-epigallochatechin, (-)-epigallochatechin gallate and pyrogallol with 2,2-diphenyl-1-picrylhydrazyl radical. *Food Chem* (2001), 73:345-349.

* cited by examiner

FIG. 3A
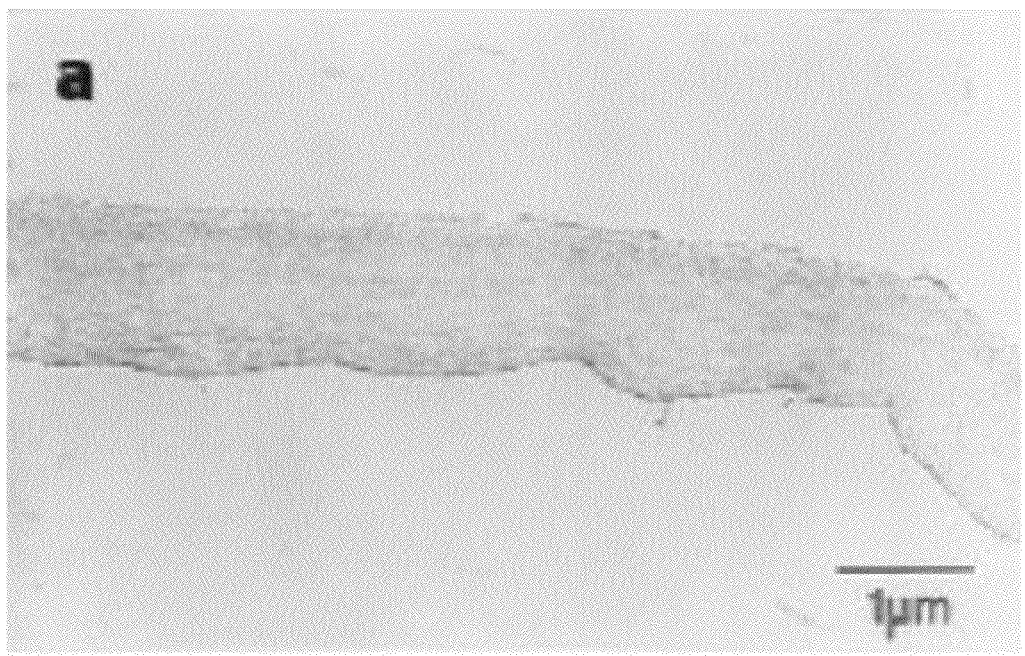
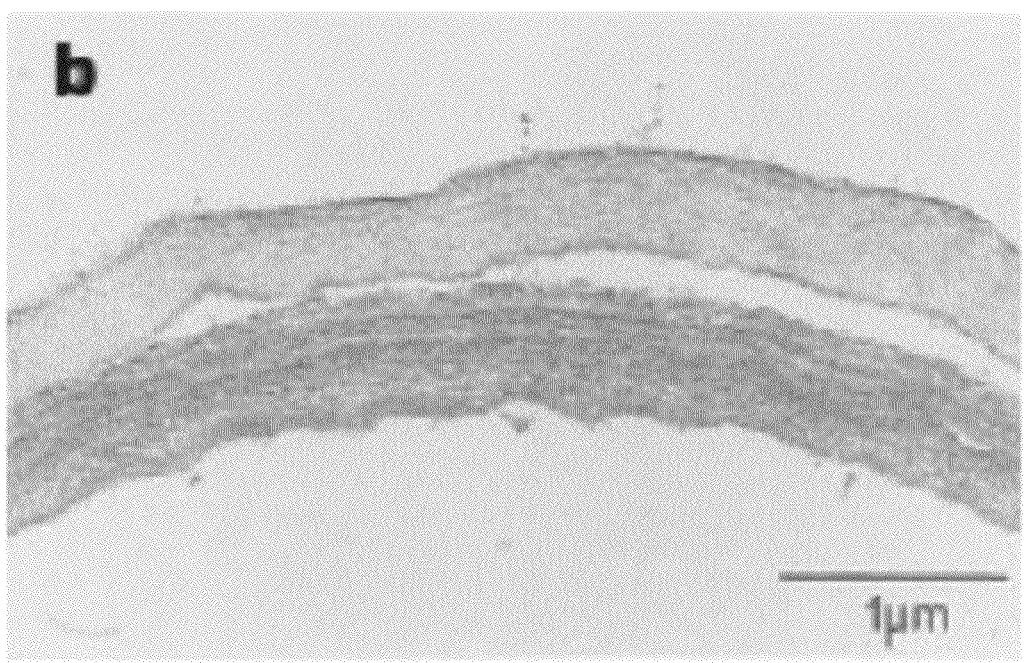
FIG. 3B

INCORPORATION OF FLAVAN-3-OLS AND GALLIC ACID DERIVATIVES INTO LIGNIN TO IMPROVE BIOMASS UTILIZATION

CROSS-REFERENCE TO RELATED APPLICATION

Priority is hereby claimed to provisional application Ser. No. 61/325,695, filed Apr. 19, 2010, which is incorporated herein.

REFERENCES

Full citations to the references referenced herein are included at the end of the Detailed Description and also at the end of the Examples. All of the referenced cited herein are incorporated herein by reference.

INTRODUCTION

Lignin is a highly complex, heterogeneous polymer found in all vascular plants. It rigidifies plants and plays a crucial role in water transport. Lignin is notable for its complex structure. It is comprised predominately from three monomers, p-coumaryl alcohol, coniferyl alcohol, and sinapyl alcohol, and a host of other structurally related monomers. See FIG. 1, which illustrates the typical monomers found in natural lignins. Hydroxycinnamaldehydes and their corresponding hydroxybenzaldehydes are found in all lignins. Hydroxycinnamyl acetates are found in most hardwoods and present in high levels in kenaf and palms. Hydroxycinnamyl p-hydroxybenzoates are found in willows, palms, poplars, and aspens. Hydroxycinnamyl p-coumarates are found in all grasses. These monomers are polymerized into polymeric lignin by combinatorial radical coupling reactions. The lignification of cell walls is also notable because it is likely the single most important factor limiting the digestion of forage by ruminants, the 'saccharification' of structural polysaccharides for conversion into biofuels and chemicals and the production of cellulose-containing pulp for use in papermaking. Practically speaking, lignin is indigestible in the digestive tract of ruminants. The interfering presence of indigestible lignins limits the ability of ruminants to utilize otherwise digestible carbohydrates present in the forage they eat. Thus, there remains a long-felt and unmet need to alter lignins in such a way that improves the digestibility/fermentability of the cell wall polysaccharides to increase the nutritional content of forages. Although cost-prohibitive for feedstuffs, harsh chemical pretreatments are commonly used to break lignin-structural polysaccharide interactions for the industrial conversion of fibrous crops into biofuels, chemical, and paper. Thus approaches for rendering lignin more susceptible to mild pretreatments are greatly desired for reducing production costs and the environmental impact of converting fibrous biomass crops into biofuels, chemicals, and paper products.

Over the past decade it has become apparent that the metabolic malleability of lignification, the process of polymerization of phenolic monomers to produce lignin polymers, provides enormous potential for engineering the troublesome polymer to be less inhibitory to structural polysaccharide utilization. Massive compositional changes can be realized by perturbing single genes in the monolignol pathway, particularly the hydroxylases.[1-4] More strikingly, monomer substitution in the process of lignification is now well authenticated,[1,2] particularly in cases where a plant's ability to biosynthesize the usual complement of monolignols is compromised. The chemical nature of lignification, involving combinatorial radical coupling of monomers (primarily with the growing polymer) without direct enzymatic control, allows compatible phenolic compounds present in the cell wall (CW) during lignification to be incorporated into the "lignin" polymer. Novel (non-monolignol) monomers available to the plant, discovered in lignins from studies on down-regulating genes in the monolignol pathway, include products of incomplete monolignol biosynthesis such as 5-hydroxyconiferyl alcohol (COMT-deficiency), and coniferaldehyde and sinapaldehyde (CAD-deficiency).[5] These compounds couple integrally (via a radical route) into the polymer in angiosperms. The list of other compounds found integrated into lignins in normal and/or transgenic plants is growing.[2,6,7] Many of the monomers currently implicated in lignification are shown in FIG. 1.

Observations to date have allowed the present inventors to detail the ideal properties of monolignol substitutes.[8] When such compounds are introduced into lignins, even at significant levels, the plants show no obvious growth/development phenotype. Monomers that have accessible conjugation into the sidechain allowing for so-called "endwise" β-O-4-coupling seem to fare the best. Examples are: 5-hydroxyconiferyl alcohol, the hydroxycinnamaldehydes, hydroxycinnamate esters, and acylated hydroxycinnamyl alcohols. See FIGS. 2a, 2b, 2c, and 2d, respectively. Due to incompatibilities in radical coupling reactions, p-hydroxyphenyl moieties fare less well than guaiacyl or syringyl moieties, at least when incorporating into guaiacyl-syringyl lignins, but other phenolics have not been well studied.

Replacing the entire monomer component of lignification with a novel monomer is unlikely to be an effective strategy that is "acceptable" to the growing plant. Introducing strategic monomers into the normal monolignol pool is, however, a viable proposition as shown by the Examples described herein. Incorporation of up to 30% novel monomer as described herein has produced plants with no pleiotropic effects or obvious growth phenotypes. Incorporation of up to 60% novel monomer has been accomplished. A range of alternative monomers are shown herein to be consistent with maintaining the plant's structural and functional integrity. Thus, the crux of the present invention is a method of manufacturing modified lignin using monomer substitution (as well as the resulting modified lignin polymer itself). The resulting modified lignin drastically eases cell wall saccharification and fermentability, both prior to and following relatively mild chemical pretreatments.

SUMMARY OF THE INVENTION

Disclosed and claimed herein is a method of manufacturing modified lignin. The method comprises conducting a lignin-producing polymerization reaction in the presence of one or more polymerizable monomers selected from the group consisting of:

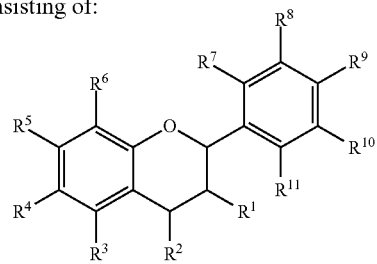

wherein $R^1$ and $R^2$ are independently selected from the group consisting of hydrogen, hydroxy, alkyloxy, alkanoyl, alkanoyloxy, hydroxy-substituted alkoxy or alkanoyl or alkanoyloxy, benzoyloxy, and mono-, di- and tri-hydroxy-substituted benzoyloxy. In one version of the method, $R^1$ and $R^2$ are not simultaneously hydrogen.

$R^3$-$R^6$ are independently selected from the group consisting of hydrogen, hydroxy, alkyl, alkyloxy, hydroxy-substituted alkyl, and hydroxy-substituted alkoxy, provided that at least one of $R^3$-$R^6$ is hydroxy;

$R^7$-$R^{11}$ are independently selected from the group consisting of hydrogen, hydroxy, alkyl, alkyloxy, hydroxy-substituted alkyl, and hydroxy-substituted alkoxy, provided that at least one of $R^7$-$R^{11}$ is hydroxy.

In a preferred version of the method, the polymerization reaction is conducted in the presence of a polymerizable monomer wherein $R^2$ is hydrogen, and $R^1$ is:

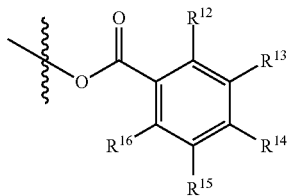

wherein $R^{12}$-$R^{16}$ are independently selected from the group consisting of hydrogen, hydroxy, alkyloxy, alkanoyl, alkanoyloxy, hydroxy-substituted alkoxy or alkanoyl or alkanoyloxy, provided that $R^{12}$-$R^{16}$ are not simultaneously hydrogen.

The polymerization reaction may also be carried out using gallate esters, such as those selected from the group consisting of:

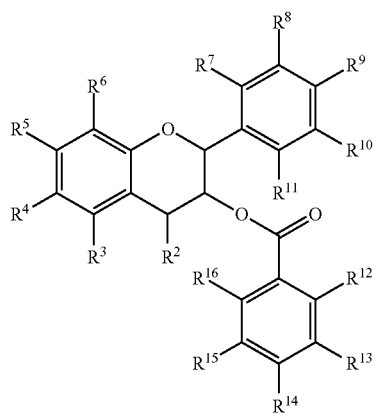

wherein $R^2$-$R^{11}$ as are defined in Claim 1, and $R^{12}$-$R^{16}$ are independently selected from the group consisting of hydrogen and hydroxy, provided that $R^{12}$-$R^{16}$ are not simultaneously hydrogen. It is preferred that at least one of, at least two of, or all three of $R^{13}$, $R^{14}$, and $R^{15}$ are hydroxy. Preferred polymerizable monomers for use in the method include catechin, epicatechin, gallocatechin, epigallocatechin, gallocatechin gallate, epigallocatechin gallate, and optical isomers thereof.

Other preferred polymerizable monomers including those wherein $R^1$, $R^3$, and $R^5$ are hydroxyl, as well as monomers wherein at least one of, at least two of, or all three of $R^8$, $R^9$, and $R^{10}$ are hydroxy.

The polymerizable monomers may also be selected from the group consisting of gallic acid and its esters, e.g., alkyl gallate, as well as polymerizable monomers selected from the group consisting of:

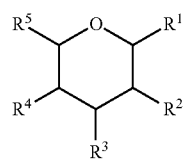

wherein $R^1$-$R^5$ are independently selected from the group consisting of hydrogen, hydroxy, =O, hydroxy, alkyloxy, alkanoyl, alkanoyloxy, hydroxy-substituted alkoxy or alkanoyl or alkanoyloxy, benzoyloxy, and mono-, di- and tri-hydroxy-substituted benzoyloxy, provided that at least one of $R^1$-$R^5$ is hydroxyl, and $R^1$-$R^5$ are not simultaneously hydrogen. See FIG. 6.

The method may be conducted in the present of, or the specific absence of certain other polymerizable monomers, such as the polymerizable monolignols as depicted in FIG. 1.

It is generally preferred that from about 10% by wt to about 60% by wt of the polymerizable monomers are reacted in the polymerization reaction, although ranges above and below the stated range are explicitly within the scope of the method (e.g., from 1 wt % to 100 wt %).

The polymerization reaction may be conducted in vitro or in vivo.

Explicitly included within the scope of the invention are modified lignins produced by the method disclosed herein.

Also disclosed herein are isolated lignified cell walls containing a compound as recited above, wherein the compound is incorporated into the lignin of the cell wall. Likewise disclosed herein are isolated plant cells containing a compound as recited above, wherein the compound is incorporated into lignin in cell walls of the isolated plant cells.

The plant cells themselves may be derived from any species of the Plantae kingdom that is now known to make lignin naturally, is discovered in the future to make lignin naturally, or does not make lignin naturally, but has been genetically modified to make lignin, without limitation. The plant cells may also be derived from plants that have been genetically modified for other purposes. This includes vascular plants of all description, monocots and dicots, hardwood and softwood trees, shrubs, grasses, grains, fruits, vegetables, etc.

The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$-$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloalkyl."

The term "alkenyl" means an alkyl group as defined above containing one or more double bonds. Examples of alkenyl groups include vinyl, 2-propenyl, crotyl, 2-isopentenyl, 2-(butadienyl), 2,4-pentadienyl, 3-(1,4-pentadienyl), etc., and higher homologs and isomers.

The term "alkynyl" means an alkyl or alkenyl group as defined above containing one or more triple bonds. Examples of alkynyl groups include ethynyl, 1- and 3-propynyl, 3-butynyl, and the like, including higher homologs and isomers.

The terms "alkylene," "alkenylene," and "alkynylene," alone or as part of another substituent means a divalent radical derived from an alkyl, alkenyl, or alkynyl group, respectively, as exemplified by —CH$_2$CH$_2$CH$_2$CH$_2$—.

"Substituted" refers to a chemical group as described herein that further includes one or more substituents, such as lower alkyl, aryl, acyl, halogen (e.g., alkylhalo such as CF$_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkenyl, alkynyl, alkylene, alkenylene, and alkynylene moieties. Additionally, these groups may be pendent from, or integral to, the carbon chain itself.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted aryl" refers to aryl as just described including one or more functional groups such as lower alkyl, acyl, halogen, alkylhalo (e.g., CF$_3$), hydroxy, amino, alkoxy, alkylamino, acylamino, acyloxy, phenoxy, mercapto, and both saturated and unsaturated cyclic hydrocarbons which are fused to the aromatic ring(s), linked covalently or linked to a common group such as a diazo, methylene, or ethylene moiety. The linking group may also be a carbonyl such as in cyclohexyl phenyl ketone. The term "substituted aryl" encompasses "substituted arylalkyl."

The term "acyl" is used to describe a ketone substituent, —C(O)R, where R is substituted or unsubstituted alkyl, alkenyl, alkynyl, or aryl as defined herein. The term "carbonyl" is used to describe an aldehyde substituent. The term "carboxy" refers to an ester substituent or carboxylic acid, i.e., —C(O)O— or —C(O)—OH.

The term "halogen" or "halo" is used herein to refer to fluorine, bromine, chlorine and iodine atoms.

The term "hydroxy" is used herein to refer to the group —OH.

The term "amino" is used to designate NRR', wherein R and R' are independently H, alkyl, alkenyl, alkynyl, aryl or substituted analogs thereof. "Amino" encompasses "alkylamino," denoting secondary and tertiary amines, and "acylamino" describing the group RC(O)NR'.

The term "alkoxy" is used herein to refer to the —OR group, where R is alkyl, alkenyl, or alkynyl, or a substituted analog thereof. Suitable alkoxy radicals include, for example, methoxy, ethoxy, t-butoxy, etc. The term "alkoxyalkyl" refers to ether substituents, monovalent or divalent, e.g. —CH$_2$—O—CH$_3$ and —CH$_2$—O—CH$_2$—.

The chemical structures shown in the figures and drawings purposefully do not designate stereochemistry and thus encompass any and all stereoisomers, e.g., racemates, diastereomers, epimers, etc., either isolated, enriched, or mixed in any combination. Trivial names are used herein to denote all stereoisomers of the stated compound unless explicitly stated to the contrary. Thus, for example, as used herein, the terms "epicatechin," "epigallocatechin," and "epigallocatechin gallate" explicitly encompass catechin, gallocatechin, and gallocatechin gallate.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

BRIEF DESCRIPTION OF THE DRAWINGS

FIG. 2a: Normal hydroxycinnamyl alcohol radicals B cross-couple with the phenolic end of the growing polymer A, mainly by β-O-4 coupling, to produce an intermediate quinone methide which rearomatizes by nucleophilic water addition to produce the elongated lignin chain A-B. The subsequent chain elongation via a further monolignol radical C etherifies the unit created by the prior monomer B addition, producing the 2-unit-elongated polymer unit A-B-C. FIG. 2b: Various γ-acylated monolignols cross-couple producing analogous products but with the β-ether unit B γ-acylated in the polymer unit A-B-C. FIG. 2c: Hydroxycinnamaldehydes B may also cross-couple with the phenolic end of the growing polymer A, again mainly by β-O-4 coupling, to produce an intermediate quinone methide, but one which rearomatizes by loss of the acidic β-proton, producing an unsaturated cinnamaldehyde-β-O-4-linked B end-unit. Incorporation further into the polymer by etherification is analogous to FIG. 2a. FIG. 2d: 5-Hydroxyconiferyl alcohol monomer A also cross-couples with the phenolic end of the growing polymer A, mainly by β-O-4-coupling, to produce an intermediate quinone methide which rearomatizes by nucleophilic water addition to produce the elongated lignin chain A-B bearing a novel 5-hydroxyguaiacyl phenolic end-unit. The subsequent chain elongation is via a further monolignol radical C coupling β-O-4 to the new phenolic end of A-B, but this time rearomatization of the quinone methide (not shown) is via internal attack of the 5-OH, producing novel benzodioxane units B-C in the 2-unit-elongated polymer unit A-B-C. 5-Hydroxyconiferyl alcohol incorporation produces lignin with a structure that deviates significantly from naturally occurring lignin. Bolded bonds are formed in the radical coupling steps.

FIGS. 3a and 3b. Biomimetically lignified cell walls. FIG. 3a: before lignification. FIG. 3b: after lignification. Importantly, the lignification is shown to occur within the cell wall.

FIG. 4a: Partial 2D $^{13}$C-$^1$H correlative HMQC NMR spectra of lignins from (i) the wild-type alfalfa; and (ii) the COMT-deficient transgenic alfalfa. Dashed ovals in (i) delineate the areas in which benzodioxane units H would correlate if they were present. FIG. 4b: The mechanism by which 5-hydroxyconiferyl alcohol incorporates into the lignin to produce novel benzodioxane structures H. FIG. 4c Gradient-selected 2D HMBC sub-spectra showing α-proton correlations to carbons within three bonds in β-aryl ether units A, β-5 units B, and benzodioxane units H. These spectra demonstrate that all types of lignin monomers undergo β-O-4 coupling to produce β-ethers A ($A_G$, $A_S$, and $A_{5H}$) and also glycerol units $G_{5H}$. Additionally, coniferyl alcohol and 5-hydroxyconiferyl alcohol (and sinapyl alcohol at lower contour levels) all add to the new 5-hydroxyguaiayl units formed after coupling of 5-coniferyl alcohol to form benzodioxanes $H_G$, $H_{5H}$, $H_S$. 5-Hydroxyconiferyl alcohol is clearly acting as a surrogate lignin monomer in this polymerization.

DETAILED DESCRIPTION

Figure 1:
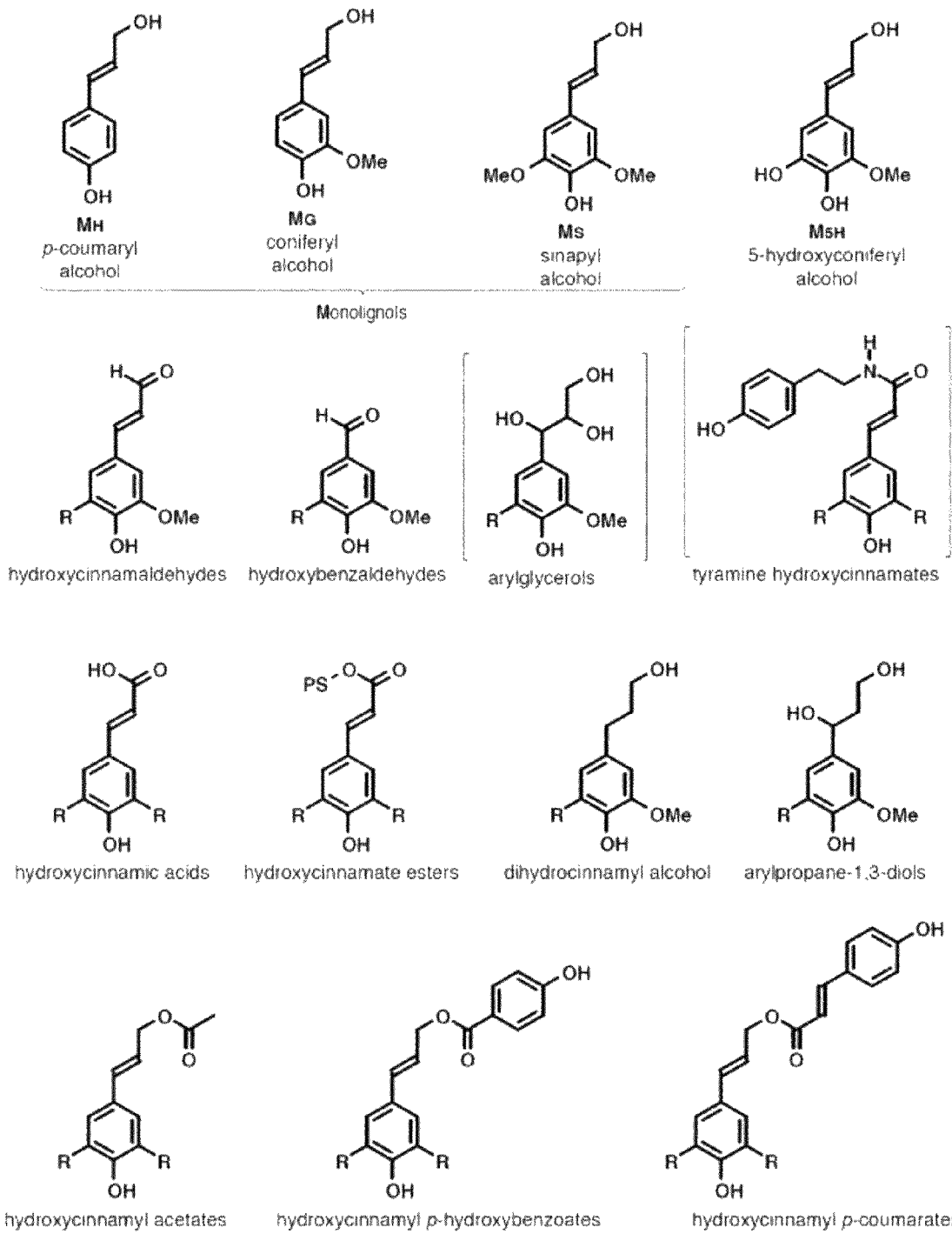
FIG. 1. Natural lignin monomers. Bracketed monomers have not been firmly established as authentic monomers, although all have been found incorporated into lignin or lignin-like plant polymers.
Figure 2A:
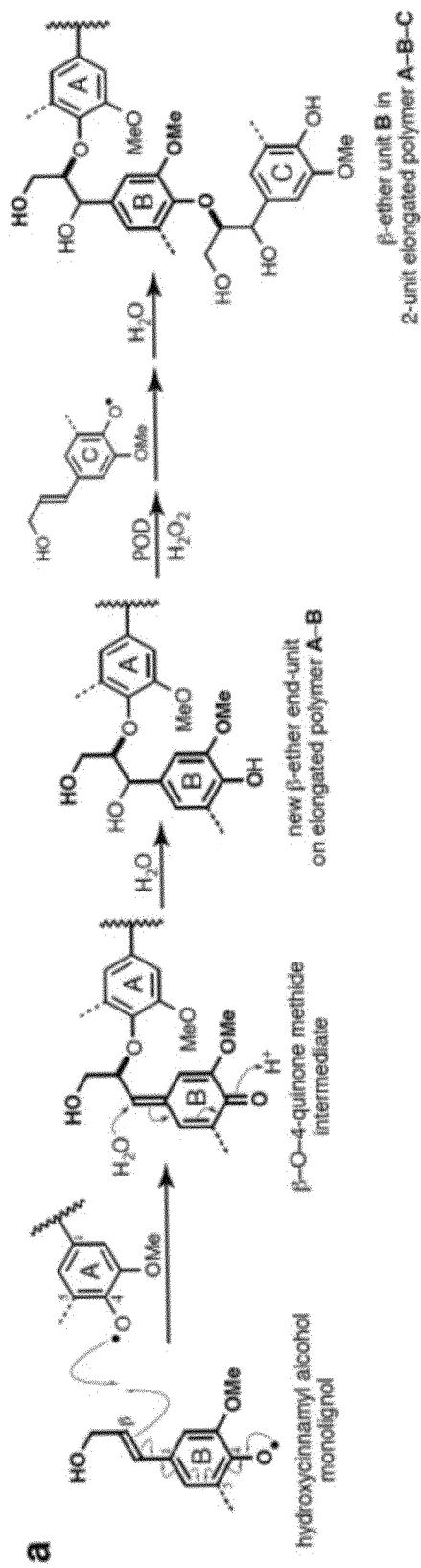
FIGS. 2a, 2b, 2c, and 2d. Exemplary monolignol substitutes. Cross-coupling and post-coupling reactions for alternative known monomers.
Figure 2B:
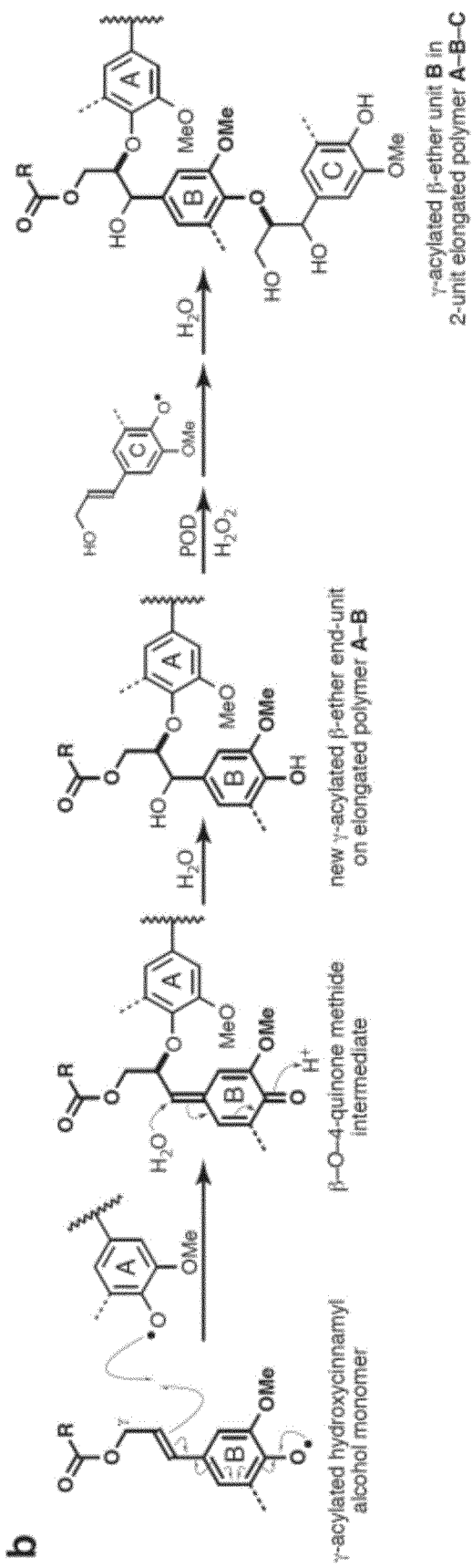
Figure 2C:
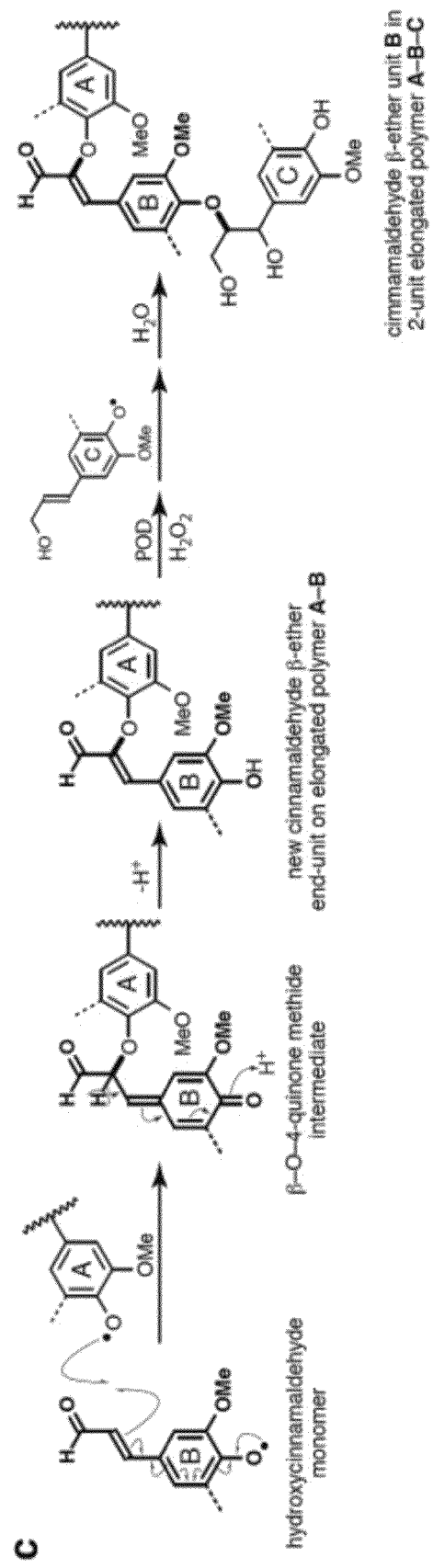
Figure 2D:
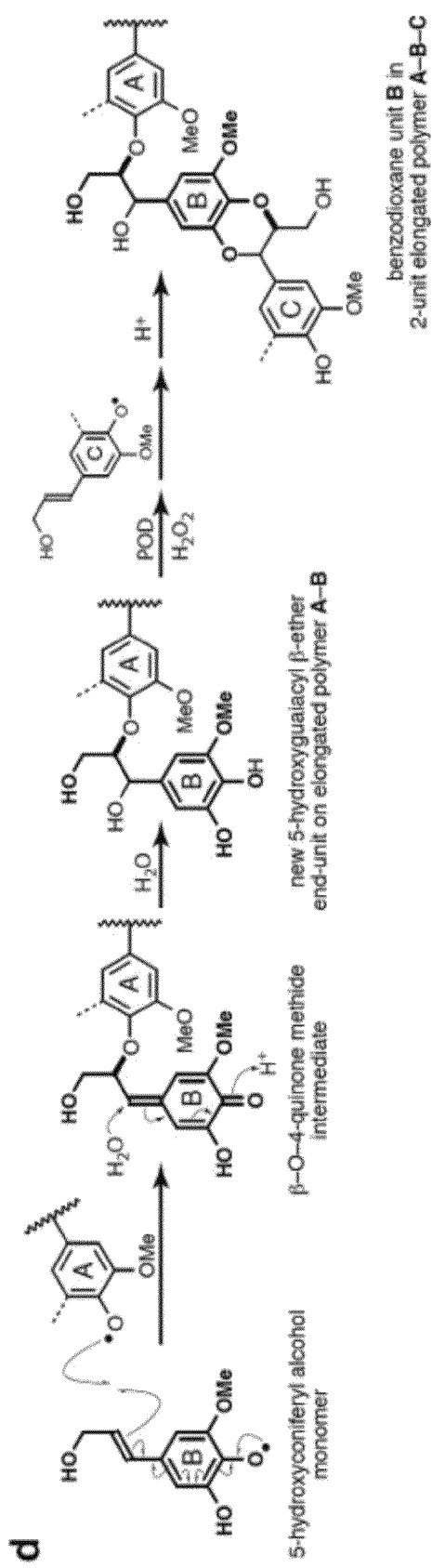

Novel monomers that appear to be well suited for lignification can be found throughout the plant kingdom. Several groups of compounds, as described below, are suitable for producing modified lignins. As a general proposition, the most suitable monomer for producing modified lignins fall into five (5) classes: (1) bifunctional monomers or monomer conjugates linked via cleavable ester or amide bonds; (2) monomers that produce novel cleavable functionalities in the lignin polymer; (3) hydrophilic monomers; (4) monomers that minimize lignin-polysaccharide cross-linking; and (5) monomers that produce simpler lignins. Each of these classes of monomers will be described below. In each instance, suitable monomers are polymerized into a modified lignin. The modified lignins are then assessed to see whether and how the modified lignins impact biomass processing in biomimetic cell wall systems.

Many of the experimental procedures referenced herein are described only briefly. Full-text references describing the known procedures can be found at: http://www.dfrc.ars.usda.gov/DFRCWebPDFs/pdfIndex.html. See also the references cited herein.

Delineate Monomer Compatibility:

Determining the compatibility of the chosen monomers with lignification via in vitro model coupling reactions is essential to determine as any selected monomer that does not couple integrally into lignins is unlikely to be valuable. Coupling and cross-coupling propensities are best tested empirically as there do not appear to be any systematic rules that predict whether a monomer will couple and cross-couple appropriately. We have used such methods to define how ferulates couple into lignins, for example.[19] The models and model polymers will also provide the NMR database required to identify how monomers incorporate into the more complex cell wall models and in transformed plants.

Biomimetically Lignify the Selected Monomers into Cell Walls:

Selected monomers, at varying levels relative to the normal monolignols, are incorporated into cell walls. Strategically $^{13}$C-labeled monomers are used as appropriate.

Delineate the Resultant Cell Wall Lignin Structure:

Structural characterization of the cell walls reveal whether the monomers integrate into wall lignins and also provide materials for conversion testing. Structures are examined by degradative methods and, most importantly, via the whole-cell-wall dissolution and NMR procedures[28] (where the strategic labeling helps reveal the bonding patterns).

Test Biomass Processing Impacts:

Monomers are selected for their potential to improve biomass processing efficiency. Artificially lignified cell walls are tested under a variety of biomass conversion methods to delineate how much improvement might be expected in planta from utilization of the monomer substitutes are various levels.

These steps are described more fully below.

Delineating Monomer Compatibility:

Synthetic in vitro coupling reactions, although they do not provide materials suitable for testing the effects of lignin modification, play a valuable role in the initial selection of potential monomers. The reasoning is simple. All the coupling reactions evidenced in lignins in vivo are also produced, admittedly at different relative levels, in vitro. If coupling and cross-coupling compatibility is not observed in synthetic coupling reactions, failure in planta is almost certainly assured because the in vivo reaction is also purely chemical. Because the monomer-substitutes are envisioned to incorporate into lignification with the normal monolignols, it is important that they be compatible with coupling and, more importantly, cross-coupling reactions with the growing polymer derived in part from those monolignols.

It is for these reasons that some suggestions, seemingly logical on paper, will simply not work. For example, it has already been established that non-methoxylated phenolic entities such a tyramine and p-coumarate do not become integrated into the polymer by coupling reactions. They are found in lignin polymers, but only as "appendages" or end-units. For example, p-coumarates are exclusively found as acylating groups in lignin sidechain γ-positions. They are free-phenolic (non-etherified), meaning that they do not undergo radical coupling reactions. On their own, in vitro, p-coumarates will couple, but what happens during lignification in the presence of normal monolignols and lignin guaiacyl/syringyl units is that radical transfer from these less-stable radicals occurs before they will enter into radical coupling.[9] Thus, lignifying with coniferyl- or sinapyl p-coumarate is known not to work. The coniferyl and sinapyl alcohol moieties incorporate as usual, but the p-coumarate end, despite being phenolic and potentially capable of radical coupling, will not incorporate—the units remain as free-phenolic pendant units.⁹ As a result, cleaving the esters will release the p-coumarate but will not cause any depolymerization of the polymer. Similarly, the idea of using tyramine ferulate will not work either; tyramine units (also non-methoxylated phenolics) do not enter into coupling reactions.²⁰ That said, if lignins are derived from higher levels of the non-methoxylated monolignol, p-coumaryl alcohol, p-coumarates and tyramines will cross-couple into those p-hydroxyphenyl-rich polymers. Thus exploring the chemical compatibility of monomers first will delineate whether it is worth introducing those monomers into C3H-deficient plants, for example— plants in which the coniferyl and sinapyl alcohol levels are depleted at the expense of the potentially compatible p-coumaryl alcohol.²¹

Although tyramine ferulate was noted as not being a candidate for introducing cleavable bonds into lignins, an analog can be found in certain plants. 3-Methoxytyramine ferulate, for example, is a bifunctional molecule in which both moieties are entirely compatible with lignification. It therefore incorporates fully, from both ends, into lignin. The cleavable amide functionality then introduced into the backbone of the polymer is exactly the kind of zipper unit that will allow such a polymer to be more readily depolymerized.

Biomimetic Lignification into Suspension-Cultured Cell Walls:

Once the monomers have been obtained/synthesized, they are then tested for their lignifying ability. As a general rule, it is not preferred to make synthetic lignins by simple in vitro polymerization of these monomers (with or without the traditional monomers) because the in vitro materials give little insight into the behavior of the cell wall during biomass processing. It is much preferred to produce cell walls lignified with the novel monomers (either in the presence of, or the absence of the normally present monolignols). A suspension-cultured corn system for producing cell walls amenable to controlled lignification by exogenously supplying the lignin monomers has been described in reference 22, incorporated herein by reference. See FIGS. 3a and 3b, which illustrate a maize cell prior to lignification (FIG. 3a) and after lignification (FIG. 3b). The cell walls already contain the polysaccharide complement, and contain their own peroxidases. Compatible phenolic monomers and a supply of $H_2O_2$ are the only requirements to effect in muro lignification. When normal monolignols are fed, the lignins are structurally extremely similar to those in the analogous growing plant.²² A representative protocol is as follows: Primary cell walls (~1.2 g dry weight) isolated from 14 d old maize cell suspensions were stirred in 120 mL of HOMOPIPES buffer (25 mM, pH 5.5 with 4 mM $CaCl_2$) and artificially lignified over ~24 h by adding separate solutions of lignin precursors (250 mg in 70 mL of 35% (v/v) dioxane:water) and $H_2O_2$ (30%, 225 μL in 90 mL water, 1.1 eq) at 3 mL/h. In two separate runs of the experiment, guaiacyl-type lignin precursors consisting of 0, 20, 40, 60% and perhaps 100% (depending on the monomer), by weight, of monomer-substitute of interest mixed with coniferyl alcohol. Introduction of novel monomers into mixed syringyl-guaiacyl-based lignins (to better mimic lignification in dicots) are run in parallel. Nonlignified controls are stirred in a solvent mixture similar to the final makeup of the lignification reaction media. Cell wall peroxidase activity during lignification is monitored with guaiacol-$H_2O_2$ staining. Although ideal for grasses, this system likely underestimates the improvements that can be realized; for example, in chemical pulping, grass cell walls are already significantly more alkali-soluble than in angiosperms (and other dicots in general) or gymnosperms. It is therefore also planned to implement and use similar suspension-cultured systems such as the secondary wall producing systems from tobacco,²³ poplar,²⁴ as well as Wagner's pine tracheary element system.²⁵ Such systems provide assorted lignified plant cell walls.

Delineating Resultant Lignin Structure:

An important aspect of this work is in establishing how well the novel monomer incorporated into lignin. With model data from the model coupling reactions in B.1 above, NMR methods in particular, and degradative methods such as analytical thioacidolysis²⁶ and the DFRC method,²⁷ enable delineating how well incorporated a novel monomer becomes, and into what types of structures it is incorporated. This provides particularly important data for delineating whether plant alteration has been successful.

Figure 4A:
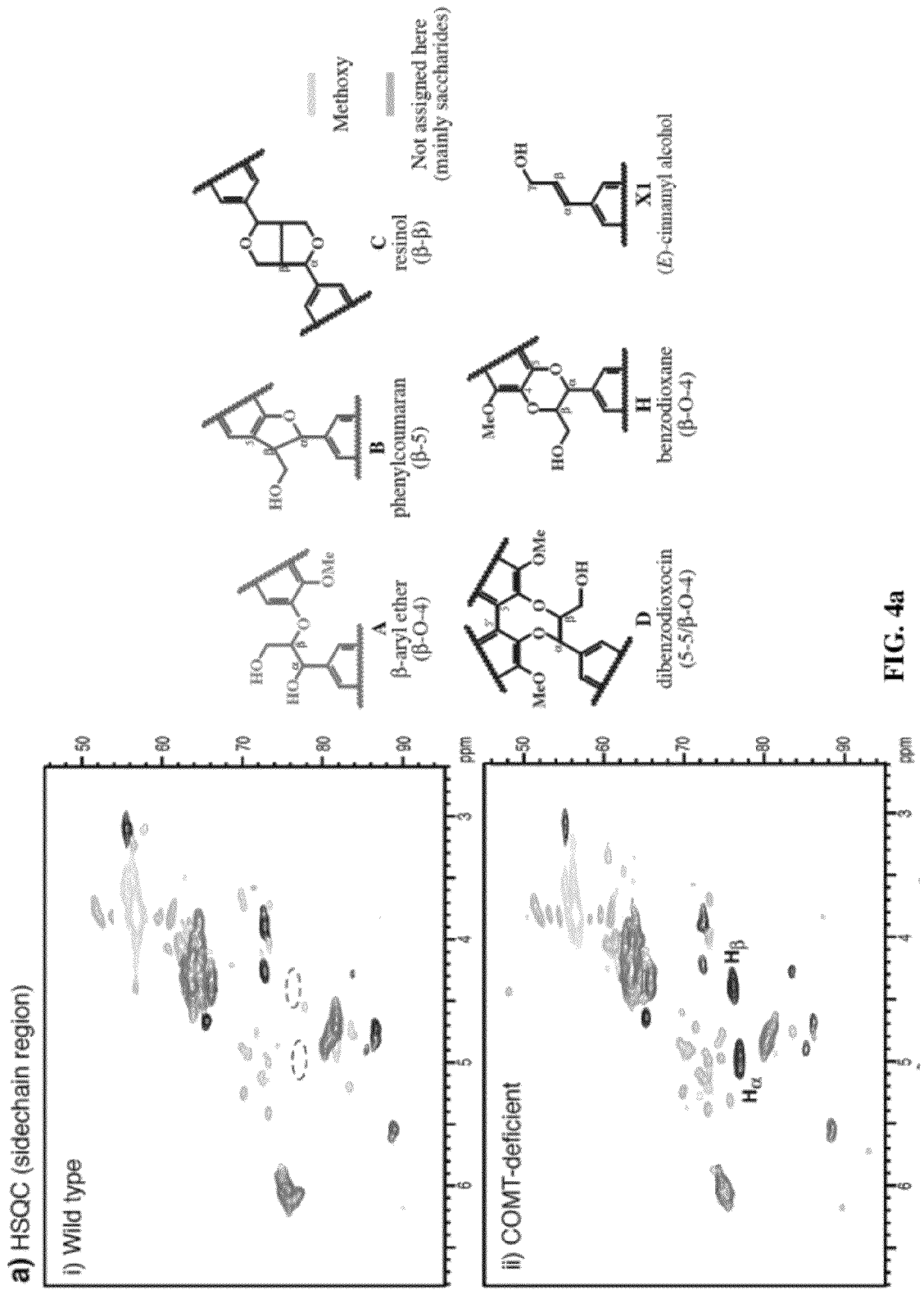
FIGS. 4a, 4b, and 4c. Examples of using NMR for identifying monolignol substitutes incorporated into lignin. COMT-deficient alfalfa substitutes 5-hydroxyconiferyl alcohol for sinapyl alcohol in the lignin polymerization reaction.
Figure 4B:
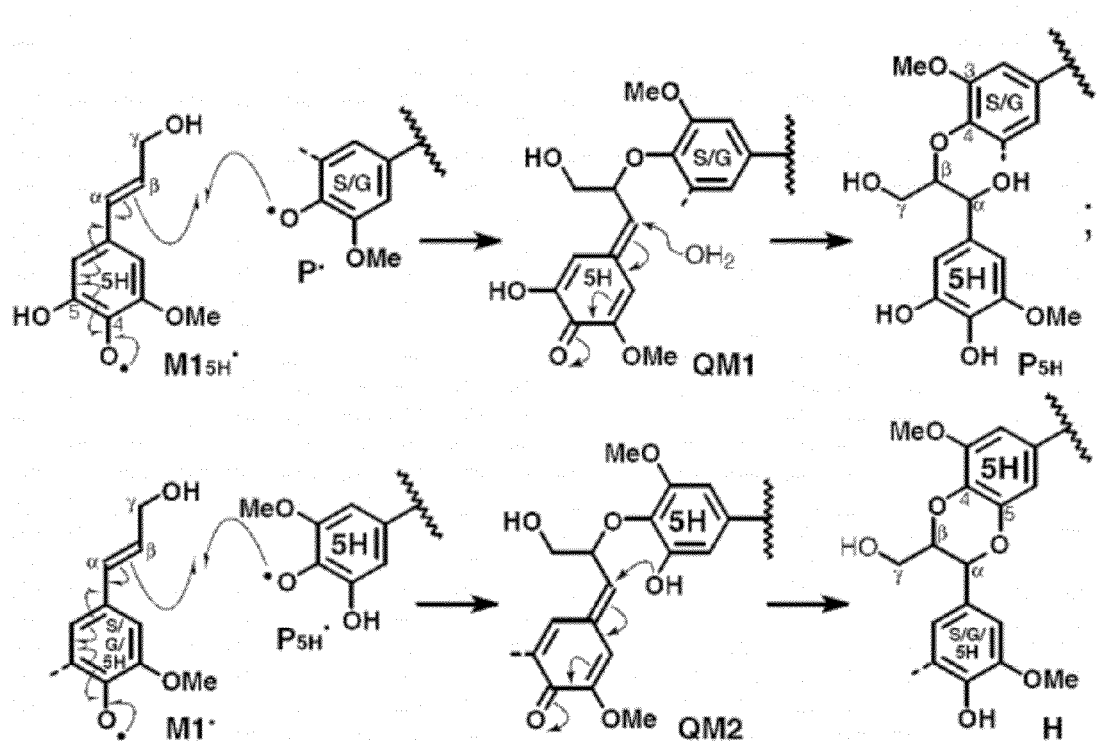
Figure 4C:
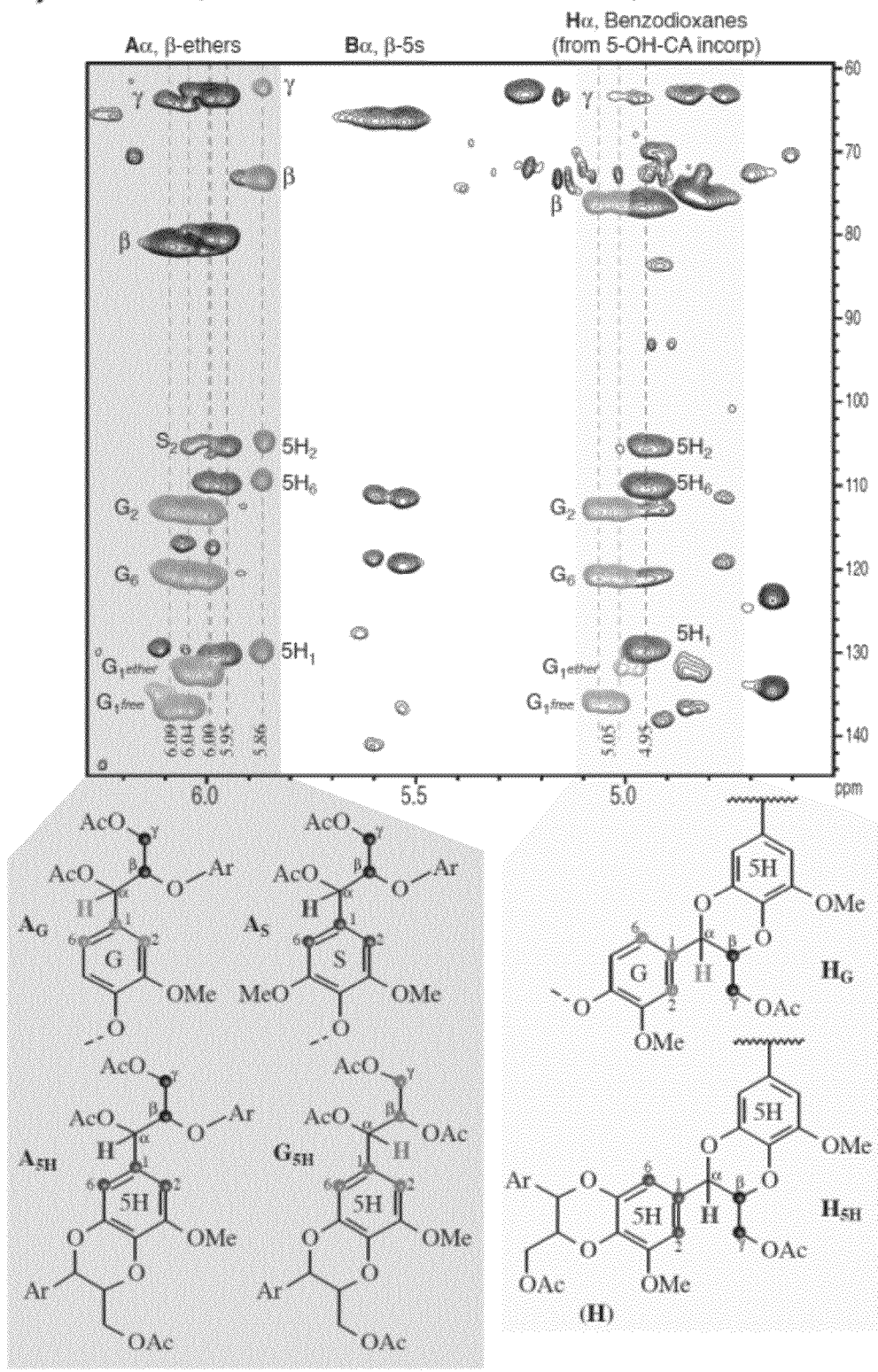

For example, FIGS. 4a, 4b, and 4c illustrate various methods to elucidate how hydroxycinnamaldehydes incorporate into CAD-deficient angiosperms, and how 5-hydroxyconiferyl alcohol incorporates into COMT-deficient angiosperms. In both instances, detailed NMR data showed not only the incorporation but revealed the detailed incorporation profiles. Using this date, the present inventors were able to discover valuable marker compounds for monitoring such incorporation.

In addition to carefully evaluated individual spectra, emerging cell wall 2D NMR "fingerprint" profiles²⁸ and chemometrics methods²⁹,³⁰ can be used to relate the detailed structural information available in the profile to various conversion parameters.

Testing Biomass Processing:

More straightforward but no less important is the processing and testing of the cell walls with modified lignins to assess the impact of the lignification changes on biomass conversion efficiency. These processes are all well established and won't be detailed herein, for example, the ethanolysis process for producing cellulose that is ideal for saccharification and fermentation.³¹

Figure 5:
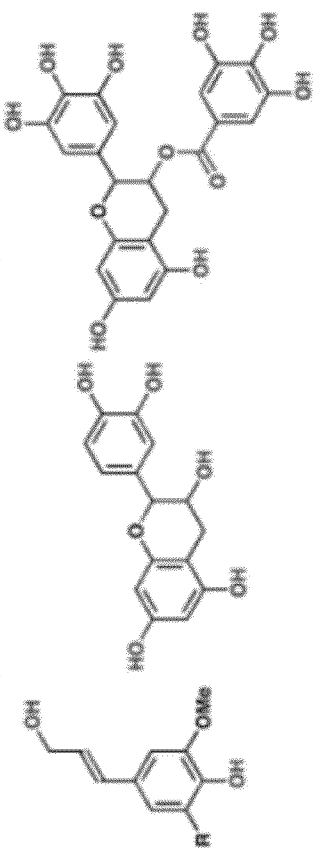
FIG. 5. Histogram depicting alkali extractability of modified lignin according to the present invention as compared to natural lignin. See the Detailed Description for experimental details. As can be seen from the figure, an increase in the number of phenolic hydroxy groups in the replacement monomer positively correlates with increased alkaline extractability. This is a highly desirable outcome because lignin extractability in alkali solutions depends on the ability to cleave the lignin polymer into smaller pieces and the solubility of the resulting fragments in the extraction solution. The increased number of phenolic hydroxyl groups in the modified lignin presumably enables larger fragments of the modified lignin to be solubilized and separated from the other components of the cells wall.
Figure 5:
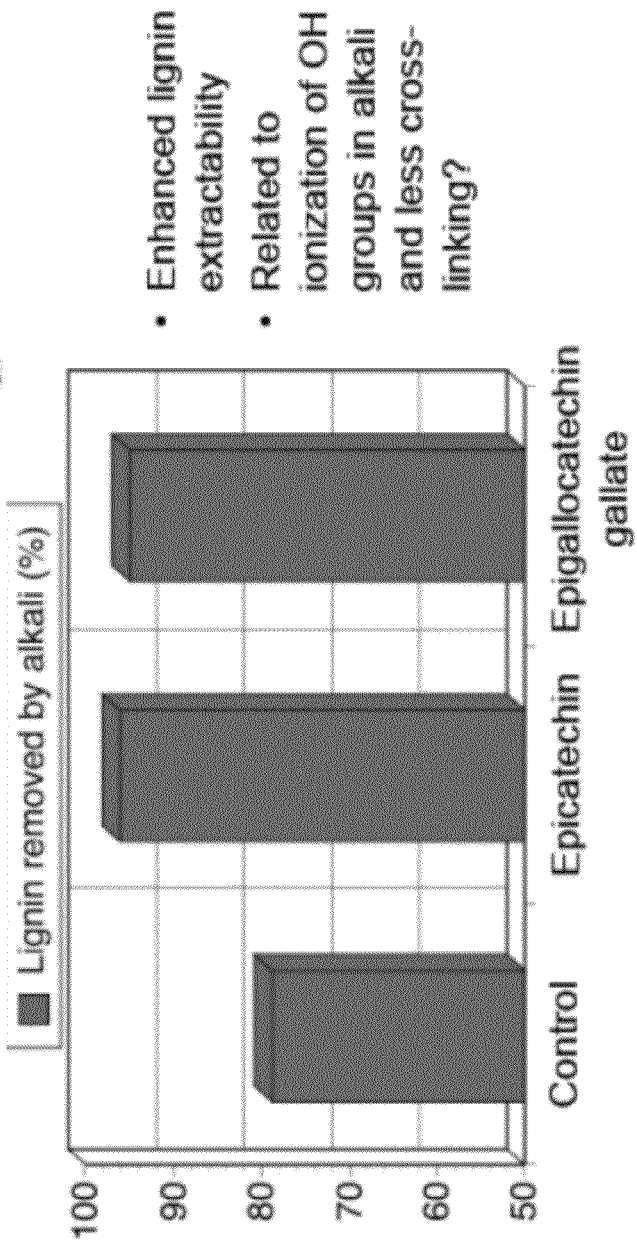
Figure 6:
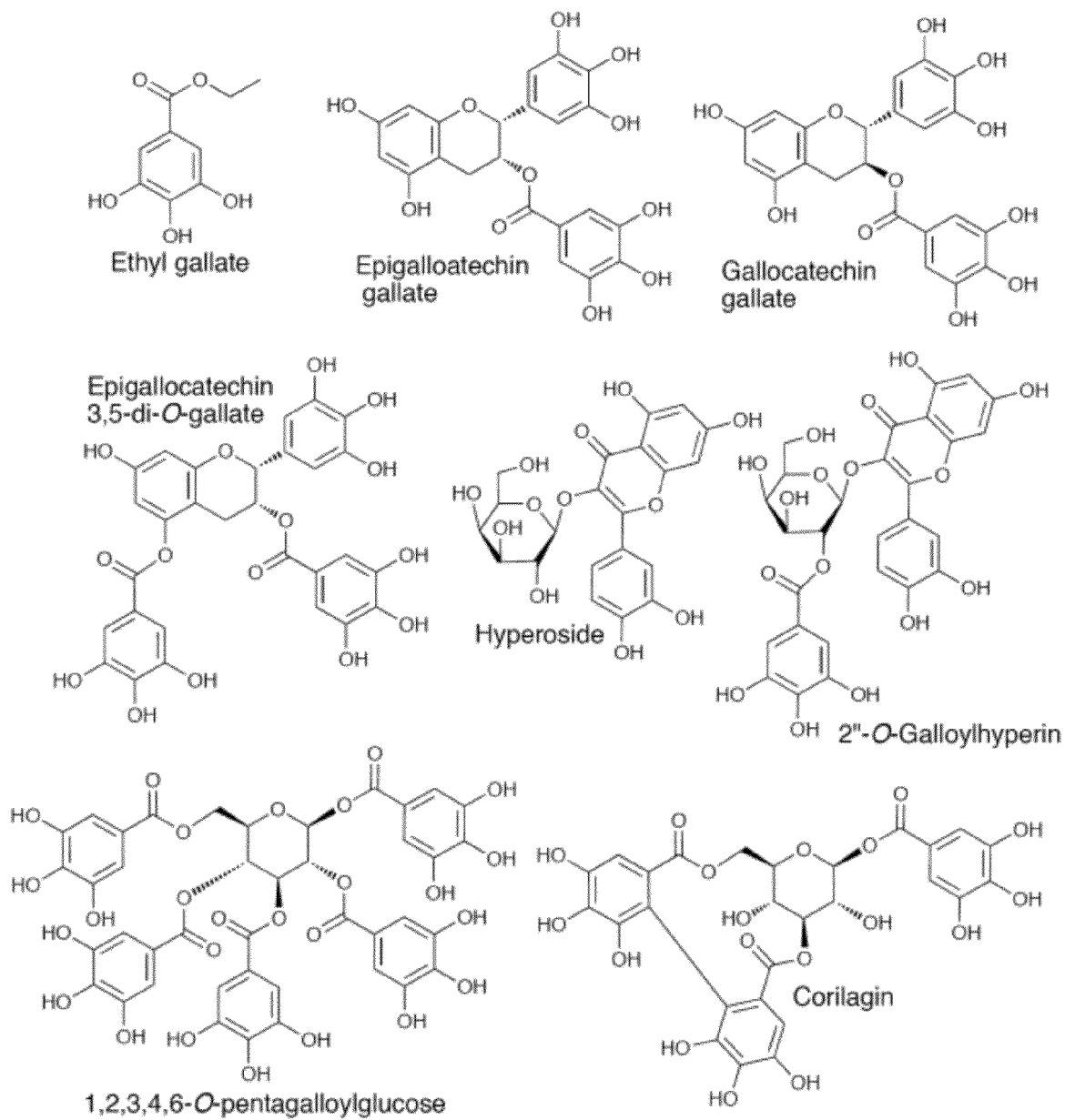
FIG. 6. Other monomers that may be used to make the modified lignin described herein. Included are gallate esters and closely related compounds such as ethyl gallate, epigallocatechin gallate, gallocatechin gallate, epigallocatechin-3,5-di-O-gallate, hyperoside, 2"-O-gallohyperin, 1,2,3,4,6-O-pentagalloylglucose, and corilagin.

The walls from above will be subjected to various biomass processing conditions, and compared to controls. To develop a comprehensive database of conditions, at least the following processing pretreatments should be tested: ethanolysis³¹ (and other organosolv methods), aminolysis, including the AFEX (ammonia fiber explosion) process,³² alkaline pulping, and acid hydrolysis. An example protocol for processing via alkaline pulping is as follows: The alkaline solubility of lignins is determined by incubating cell walls under $N_2$ atmosphere with 100 mL/g of 0.5 M aqueous NaOH for 22 h at 30° C. or for 2.5 h at 100 or 160° C. Anthraquinone (0.02 mg/mL) is added to catalyze the hydrolysis of lignin ether inter-unit linkages at 160° C. After cooling, alkaline residues are pelleted (5,000×g, 15 min), resuspended in water, neutralized with acetic acid, and then repeatedly pelleted (5,000×g, 15 min) and resuspended in water before freeze-drying and weighing. Original cell walls and alkaline residues are analyzed for lignin by the acetyl bromide method. Alkaline hydrolysates are extracted into ethyl acetate containing 50 mM QAM, dried, and dissolved in THF to determine the molecular weight distribution of by SEC-HPLC. An example is shown in FIG. 5, comparing the lignin extractability of a control lignin vs. a lignin fabricated using epichatechin monomers and a lignin fabricated using epigallocatechin gallate. (The modified lignins were made using the corn system described hereinabove.) As can be seen from FIG. 5, the modified lignins had significantly increased extractability. Various GC-MS analyses may also be performed depending on the monomer used. Enzymatic saccharification and simultaneous saccharification and fermentation will be compared on the products from these pretreatments, as well as directly on steam exploded material. One of the most convenient and high-throughput measures of ruminal fermentability, a gas-accumulation in vitro method, has been shown to correlate well with the fermentability of cellulosic biomass to ethanol (via simultaneous saccharification and fermentation).
Utility:

As shown in the Examples below, the initial results are quite favorable. Such gains portend enormous potential for sustainable local (and even small-scale) processing without massive facility costs. (A conventional pulp mill digester facility currently costs ~$1 billion, for example.) Decreasing the need to transport low-density plant materials across large distances, by processing toward higher-density materials locally, can also be a huge factor in decreasing the total energy requirements of processing, with consequent major impact on reducing greenhouse emissions, particularly if fossil fuels remain in (partial) use for transport. These lignin-modified materials appear to be exactly what this industry require. The present method thus has the potential to deliver quantum improvements in biomass processing compared to the more incremental changes that are envisioned from simply perturbing the known lignin monomer pathways.

In summary, the present method structurally alters lignin by altering its monomer complement to allow the biomass polysaccharides to be more efficiently and sustainably utilized.

EXAMPLES

The following Examples are included solely to provide a more complete disclose of the invention disclosed and claimed herein. The Examples do not limit the scope of the claimed invention in any fashion.

As noted above, recent discoveries highlighting the metabolic pliability of plant lignification indicate that lignin can be engineered to dramatically alter its composition. Perturbing single or multiple genes in the monolignol pathway of angiosperms can lead to dramatic shifts in the proportions of normal monolignols (e.g., coniferyl 1 and sinapyl alcohol 2) and pathway intermediates polymerized into lignin [1, 2]. The malleability of lignification is further illustrated in some angiosperms by the pre-acylation of monolignols with acetate, p-hydroxybenzoate, or p-coumarate [1, 36] and the oxidative coupling of ferulate and diferulate xylan esters into lignin [9, 37, 38].

Recent efforts in lignin bioengineering are primarily aimed at manipulating the normal monolignol biosynthetic pathway [39], but apoplastic targeting of phenolics from other metabolic pathways provides exciting opportunities for designing lignin that is less inhibitory toward polysaccharide fermentation or easier to remove by biological or chemical pretreatments. Model studies conducted by the present inventors using maize cell walls demonstrated that partial substitution of coniferyl alcohol with coniferyl ferulate (an ester conjugate from lignan biosynthesis) dramatically enhanced the alkaline extractability of lignin and the enzymatic hydrolysis of fiber [40]. Bioengineering of plants to copolymerize coniferyl or sinapyl ferulate with monolignols is now being pursued as a means for enhancing biomass saccharification or pulping for paper production.

To identify other promising avenues for lignin bioengineering, the present Examples were designed assess how the inclusion of phenolics derived from various metabolic pathways alter lignin formation and the utilization of plant cell walls. One path to explore is reducing the hydrophobicity of lignin to permit greater penetration and hydrolysis of fiber by polysaccharidases. Lignin hydrophobicity could be modulated by incorporating phenolics with extensive sidechain or aromatic ring hydroxylation (e.g., guaiacyl glycerol 4 or epigallocatechin gallate 11) or substituting hydrophilic groups (e.g., feruloylquinic acid 8 or 1-O-feruloyl glycerol 14). Another approach is to incorporate phenolics with ortho-diol functionality (e.g., methyl caffeate 5, caffeoylquinic acid 6, epicatechin 9, epigallocatechin 10, and epigallocatechin gallate 11). The presence of such o-diphenols provides an intramolecular pathway to trap lignin quinone methide intermediates which form cross-links between lignin and structural polysaccharides [8]; such cross-links appear to limit the enzymatic hydrolysis of cell walls [41, 42]. Another route, first illustrated by the present inventors with coniferyl ferulate [40], is to incorporate readily cleaved bi-phenolic conjugates (e.g., epigallocatechin gallate 11, 1,3-di-O-feruloyl glycerol 15, or 1,4-di-O-feruloyl threitol 16) to facilitate lignin depolymerization during pretreatment of biomass for saccharification.

In this study, a well-characterized biomimetic cell wall model was used [43] to explore how various monolignol substitutes influence the formation of lignin and the in vitro fermentability of cell walls by rumen microflora as determined by the analysis of residual nonfermentable polysaccharides (NP) and by monitoring gas production. Because gas production is directly linked to structural carbohydrate fermentation [44, 45] and highly correlated with biomass fermentation to ethanol [46], the results have broad application in plant selection and engineering programs aimed at improving feed utilization by livestock and biomass conversion into biofuels.
Methods:
General:

Quinic acid, ferulic acid, and other reagents were obtained from Aldrich. NMR spectra of synthesized compounds were run on a Bruker (Billerica, Mass.) DRX-360 fitted with a 5 mm 1H/broadband gradient probe with inverse ($^1$H-detected) geometry. The solvent used for synthetic compounds was acetone-$d_6$ unless otherwise specified; referencing was to the central solvent peak ($\delta_C$ 29.80, $\delta_H$ 2.04 for acetone).
Preparation of Monolignols and Monolignol Substitutes:

Coniferyl alcohol 1, sinapyl alcohol 2, dihydroconiferyl alcohol 3, guaiacyl glycerol 4, methyl ferulate 7, and ethyl ferulate 12 were synthesized as described previously [10, 11, 47, 48]. Methyl caffeate 5, caffeoylquinic acid 6, epicatechin 9, epigallocatechin 10, and epigallocatechin gallate 11 were obtained from commercial sources (Sigma [St. Louis, Mo.] or Indofine [Hillsborough, N.J.]).

5-Feruloylquinic Acid 8:

The synthesis follows that of chlorogenic acid (caffeoylquinic acid 6) and other analogs described by Hemmerle et al. [49]. Briefly, methyl ferulate 7 was protected via reaction with 2-(trimethylsilyl)ethoxymethyl chloride to give compound 17 as an orange oil, which was saponified directly to give 18 as a solid (58% of theoretical yield based on methyl ferulate); recrystallization from hexane afforded colorless crystals, mp 80-83° C. The amide 19 was prepared and used directly in coupling with 23. Protection of (1R,3R,4R,5R)-(−)-quinic acid 20 with cyclohexanone gave solid 21 in 92% yield. Recrystallization from ether/hexane gave a solid with mp 142.5-143.5° C., lit. [50] mp 142-143° C. Compound 21 was also protected via reaction with 2-(trimethylsilyl)ethoxymethyl chloride to give solid compound 22 in 95% yield. Recrystallization from hexane gave a colorless solid, mp 103-105° C. The sodium salt 23 was prepared and used without purification in coupling with compound 19 to produce the required feruloyl quinic acid 8 as a foamy solid.

Cell Wall Lignification:

Nonlignified primary cell walls (~1.8 g dry weight) isolated from maize cell suspensions [22] were stirred in 250 mL of Homopipes buffer (75 mM, pH 5.5) containing 2000 units of glucose oxidase (Sigma, St. Louis, Mo. EC 1.1.3.4). Glucose (0.25 mmol in 2.5 mL of water) was added drop wise to cell wall suspensions over 30 min and then stirred for 30 min to generate $H_2O_2$ (~2 eq/mol of cell wall ferulate) for dimerizing ferulates by wall-bound peroxidases. Cell walls were artificially lignified by adding a two-component mixture of coniferyl alcohol 1 (0.6 mmol) and sinapyl alcohol 2 (0.6 mmol) or three-component mixtures of coniferyl alcohol (0.4 mmol) and sinapyl alcohol (0.4 mmol) with one of the following monolignol substitutes: dihydroconiferyl alcohol 3 (0.4 mmol), guaiacylglycerol 4 (0.4 mmol), methyl caffeate 5 (0.4 mmol), caffeoylquinic acid 6 (0.4 mmol), methyl ferulate 7 (0.4 mmol), feruloylquinic acid 8 (0.4 mmol), epicatechin 9 (0.4 mmol), epigallocatechin 10 (0.4 mmol), or epigallocatechin gallate 11 (0.2 mmol). The monolignol mixtures and glucose (1.5 mmol, to generate $H_2O_2$), prepared in 2.5 mL dioxane and 95 mL of water, were added dropwise to the cell wall suspensions over a ~20 h period.

In these studies, treatments were replicated twice in independent experiments and nonlignified controls were stirred in a solvent mixture similar to the final makeup of the lignification reaction media. Cell wall peroxidase activity at the end of monolignol addition was visually assessed with guaiacol-$H_2O_2$ staining [52]. Following additions, cell walls were stirred for an additional 24 h, pelleted (5,000×g, 15 min) and twice resuspended in 600 mL of water for 60 min, and pelleted (5,000×g, 15 min) again to remove low molecular weight dehydrogenation products. The cell wall pellets were then resuspended in 650 mL of 9:1 (v/v) acetone:water for 30 min, collected on glass-fiber filters (1.2 μm retention) and washed with 300 mL of acetone:water to remove non-bound lignins. After repeated washing with acetone, cell walls were set overnight in a hood and then dried at 55° C. and weighed.

Cell Wall Analyses:

Acid-insoluble Kiason lignin in cell wall samples (75 mg) was determined in duplicate by a two-stage hydrolysis in 12 M $H_2SO_4$ at 25° C. for 2 h followed by 1.6 M $H_2SO_4$ at 100° C. for 3 h [53]. Whole cell walls (~50 mg) from selected lignification treatments were sonicated in DMSO-$d_6$ with pyridine-$d_5$ and subjected to gel-state NMR using a Bruker Avance-500 MHz instrument as recently described [54].

Gas production during fermentation of cell walls (100 mg) at 39° C. in 60 mL sealed bottles was monitored with pressure transducers for 45 h following addition of 5.7 mL of phosphate-bicarbonate buffer, 0.3 mL of reducing agent, and 4 mL of diluted rumen inoculum [55]. Filtered inoculum was prepared with a 1:2 ratio (v/v) of rumen fluid and blended buffer-extracted rumen solids collected from two Holstein cows fed a total mixed ration of corn silage, corn grain, alfalfa hay, soybean meal, and supplemental vitamins and minerals [55]. Blank-corrected gas production data from two to four independent fermentation runs were fitted with a dual-pool logistic model to estimate the kinetics of cell wall fermentation [55]. Freeze-dried residues remaining after fermentation were dissolved in 12 M $H_2SO_4$ at 25° C. for 2 h and analyzed for NP by the phenol-sulfuric acid assay [56] with corrections for inoculum contamination and sugar recovery. The recovery of sugars from NP was estimated by running unfermented nonlignified cell walls through the 12 M $H_2SO_4$ dissolution/phenol-sulfuric acid assay procedure.

Statistical Methods:

Klason lignin and fermentation data for monolignol treatments were subjected to an analysis of variance by PROC GLM according to a randomized complete block design with two replications [57, 58]. If F-tests were significant (P 0.05), then differences among monolignol treatment means were tested by the LSD procedure (P=0.05). Unless otherwise noted, all reported treatment differences were significant at P=0.05.

Results and Discussion:

Cell Wall Lignification:

Previous work demonstrated that artificial lignins formed in primary cell walls isolated from maize cell suspensions are structurally similar to those naturally formed in grasses [22]. In the current Example, maize cell walls containing bound peroxidases were artificially lignified with normal monolignols (coniferyl and sinapyl alcohols 1, 2) added alone or in combination with various phenolic monolignol substitutes 3-16. Each monolignol substitute comprised about one-third by weight of the precursor mixture, a shift in lignin composition comparable to that often observed in mutant or transgenic plants with altered lignin biosynthesis. After dissolution in a minimal volume of dioxane, normal monolignols and most monolignol substitutes readily formed aqueous solutions.

At the conclusion of lignification, guaiacol staining indicated weak residual peroxidase activity following addition of normal monolignols with feruloyl esters, very weak to no activity with diferuloyl esters, but good activity for all other treatments (data not shown). While peroxidase activity is gradually lost during normal lignification [59], partial substitution of monolignols with feruloyl and particularly diferuloyl esters greatly accelerated this process. Among possible inactivation pathways [13, 60, 61], active site attack by ferulate phenoxy radicals or enzyme precipitation due to sorption or cross-linking to polymeric products are most plausible given the extremely high substrate preference of maize peroxidase for ferulate esters [62], the bi-phenolic cross-linking capability of diferuloyl polyol esters, and their aforementioned poor aqueous solubility.

Based on Klason lignin analysis, inclusion of feruloylquinic acid 8, methyl caffeate 5, or especially caffeoylquinic acid 6 considerably depressed lignin formation while methyl ferulate 7 readily copolymerized with monolignols to form wall bound lignin (Table 1). Methyl and quinic acid esters of ferulic and caffeic acids are plant extractives of which caffeoylquinic acid (also known as chlorogenic acid) and feruloylquinic acid are especially abundant in coffee and some other beverages and foods [63]. To tentatively investigate the cause of depressed lignification, cell walls from selected treatments were subjected to gel-state 2D NMR. Spectra of cell walls lignified with normal monolignols or monolignols plus feruloylquinic acid both contained only correlations of guaiacyl units (derived from coniferyl alcohol) and syringyl units (derived from sinapyl alcohol); the absence of ferulate correlations in the latter spectrum suggests that feruloylquinic acid was not incorporated into wall bound lignin. (Correlations for syringyl (S), guaiacyl (G), ferulic acid (FA), and epigallocatechin (EG) units in lignin were assigned using data from previous publications [77-79] and an NMR database [80].) It must, however, be pointed out that correlations of native cell wall ferulates comprising ~10% of the lignin polymer are also missing from spectra of control cell walls. Thus extensive polymerization of ferulates into a wide array of coupling products [9, 37, 38] may sufficiently disperse their correlations or shift and coalesce them with adjacent guaiacyl correlations to render them below the detection limit of these 2D NMR experiments. In any case, it seems that depressed lignin formation by this group of monolignol substitutes was associated with the presence of quinic or caffeic acid moieties and not affected by methyl or ferulate groups. Highly hydrophilic quinic acid moieties might hinder the association and copolymerization hydroxycinnamate radicals with hydrophobic lignin polymers, but this or alternative coupling reactions [66-68]. Dihydroconiferyl alcohol 3 and guaiacylglycerol 4, differing in sidechain hydroxylation, were also extensively copolymerized into lignin. These phenylpropanoids are known to cross-couple with monolignols

TABLE 1

Klason lignin, in-vitro fermentation kinetics$^a$, nonfermentable polysaccharides (NP), fermentation gas reduction (FGR)$^b$, and nonfermentable polysaccharide accumulation (NPA)$^c$ due to artificial lignification of maize cell walls with a binary mixture of coniferyl alcohol (CA) and sinapyl alcohol (SA) or a trinary mixtures of CA and SA with various monolignol substitutes.

| Monolignols | Lignin mg/g | $L_1$ (h)$^a$ | $k_1$ (h$^{-1}$)$^a$ | A (mL/g)$^a$ | $L_2$ (h)$^b$ | $k_2$ (h$^{-1}$)$^b$ | B (mL/g)$^b$ | AB (mL/g) | NP (mg/g) | FGR | NPA |
|---|---|---|---|---|---|---|---|---|---|---|---|
| Nonlignified control | — | 2.0 | 0.217 | 290 | 2.4 | 0.044 | 53 | 343 | 22 | — | — |
| CA:SA lignified control | 153 | 3.4 | 0.097 | 243 | 19.9 | 0.067 | 17 | 259 | 114 | 0.545 | 0.604 |
| CA:SA:Dihydroconiferyl alcohol | 154 | 3.0 | 0.094 | 241 | 17.6 | 0.068 | 23 | 265 | 113 | 0.508 | 0.594 |
| CA:SA:Guaiacylglycerol | 152 | 2.6 | 0.099 | 243 | 13.6 | 0.053 | 28 | 271 | 94 | 0.473 | 0.474 |
| CA:SA:Methyl caffeate | 111 | 2.1 | 0.124 | 265 | 9.1 | 0.049 | 33 | 298 | 59 | 0.406 | 0.343 |
| CA:SA:Caffeoylquinic acid | 92 | 2.1 | 0.160 | 272 | 5.3 | 0.050 | 42 | 315 | 28 | 0.308 | 0.071 |
| CA:SA:Methyl ferulate | 159 | 3.2 | 0.080 | 211 | 15.6 | 0.067 | 23 | 235 | 166 | 0.680 | 0.911 |
| CA:SA:Feruloylquinic acid | 117 | 2.8 | 0.130 | 265 | 10.7 | 0.048 | 30 | 295 | 52 | 0.410 | 0.258 |
| CA:SA:Epicatechin | 170 | 2.9 | 0.060 | 238 | 31.6 | 0.118 | 6 | 244 | 155 | 0.578 | 0.779 |
| CA:SA:Epigallocatechin | 160 | 3.1 | 0.094 | 259 | 23.3 | 0.089 | 11 | 270 | 87 | 0.455 | 0.413 |
| CA:SA:Epigallocatechin gallate | 167 | 3.1 | 0.098 | 246 | 16.6 | 0.057 | 23 | 269 | 88 | 0.443 | 0.399 |
| LSD (P = 0.05) | 12 | 0.7 | 0.015 | 16 | 9.9 | 0.036 | 17 | 14 | 21 | 0.115 | 0.120 |

$^a$Kinetic parameters: lag time ($L_1$), rate constant ($k_1$), and volume (A) of gas produced from a rapidly digested pool; lag time ($L_2$), rate constant ($k_2$), and volume (B) of gas produced from a slowly digested pool; and total gas volume (AB)
$^b$FGR per unit of lignin calculated as ($AB_{nonlignified}$ − $AB_{lignified}$)/Klason lignin
$^c$NPA per unit of lignin calculated as ($NP_{lignified}$ − $NP_{nonlignified}$)/Klason lignin mechanisms require further study. Under slightly acidic aqueous conditions, peroxidase-generated radicals of caffeate undergo homo-dimerization or cross-coupling with ferulate and sinapate [64] and thus should cross-couple with coniferyl and sinapyl alcohols derived from these acids, but in the current study these products, if formed, were poorly incorporated into polymeric wall-bound lignin. Alternatively, poor incorporation of caffeate may be due to its tendency to form quinones, which avoid radical coupling reactions characteristic of lignin formation [65].

In contrast to caffeate, Klason lignin analysis suggested other benzene diol or triols (epicatechin 9, epigallocatechin 10, and epigallocatechin gallate 11) readily formed copolymer lignins with monolignols (Table 1). Indeed, the incorporation of catechins into lignin is illustrated by diagnostic 2D gel NMR contours for epigallocatechin gallate. The catechins, which are precursors of vacuolar-deposited tannins in plants, readily form quinones and undergo radical homo- via their phenolic ring to form endgroups in softwood lignins [2].

In contrast to feruloylquinic acid, Klason lignin analysis indicated excellent incorporation of other feruloyl esters involving ethyl 12, ethylene glycol 13, or glycerol 14 groups (Table 2), despite their tendency to accelerate peroxidase inactivation. As noted previously with hydroxycinnamate-monolignols esters [40, 52], diferuloyl polyols 15 and 16 depleted peroxidase activity and depressed lignification, but they became substantial components of lignin based on diagnostic ferulate correlations in NMR spectra (data not shown). Oxidative coupling reactions of feruloyl polyol esters have not been reported, but they would likely form a wide array of ferulate, diferulate, and ferulate-monolignol structures similar to those previously observed with ethyl ferulate, ferulate-monolignol conjugates, and various ferulate-polysaccharide esters [37, 38, 40, 69-71].

TABLE 2

Klason lignin, in-vitro fermentation kinetics$^a$, nonfermentable polysaccharides (NP), fermentation gas reduction (FGR)$^b$, and nonfermentable polysaccharide accumulation (NPA)$^c$ due to artificial lignification of maize cell walls with coniferyl alcohol (CA) or a binary mixtures of CA with ethyl or various polyol esters of ferulate.

| Monolignols | Lignin mg/g | $L_1$ (h) | $k_1$ (h$^{-1}$) | A (mL/g) | $L_2$ (h) | $k_2$ (h$^{-1}$) | B (mL/g) | AB (mL/g) | NP (mg/g) | FGR | NPA |
|---|---|---|---|---|---|---|---|---|---|---|---|
| Nonlignified control | — | 1.83 | 0.244 | 298 | 0.4 | 0.033 | 67 | 365 | 21 | — | — |
| CA lignified control | 151 | 1.95 | 0.099 | 231 | 11.1 | 0.043 | 46 | 277 | 130 | 0.589 | 0.708 |
| CA:ethyl ferulate | 154 | 1.94 | 0.082 | 225 | 14.9 | 0.037 | 35 | 260 | 162 | 0.697 | 0.907 |
| CA:feruloyl ethylene glycol | 149 | 2.44 | 0.092 | 231 | 12.5 | 0.041 | 40 | 271 | 142 | 0.647 | 0.808 |
| CA:1-O-feruloyl glycerol | 149 | 2.31 | 0.114 | 221 | 9.5 | 0.040 | 48 | 269 | 122 | 0.652 | 0.676 |
| CA:1,3-O-diferuloyl glycerol | 124 | 2.33 | 0.135 | 251 | 9.4 | 0.040 | 47 | 299 | 81 | 0.544 | 0.487 |
| CA:1,4-O-diferuloyl threitol | 135 | 2.36 | 0.117 | 236 | 10.3 | 0.040 | 43 | 279 | 90 | 0.650 | 0.508 |
| LSD (P = 0.05) | 20 | 0.51 | 0.017 | 23 | 1.9 | 0.008 | 12 | 30 | 38 | NS | 0.163 |

$^a$Kinetic parameters: lag time ($L_1$), rate constant ($k_1$), and volume (A) of gas produced from a rapidly digested pool; lag time ($L_2$), rate constant ($k_2$), and volume (B) of gas produced from a slowly digested pool; and total gas volume (AB)
$^b$FGR per unit of lignin calculated as ($AB_{nonlignified}$ − $AB_{lignified}$)/Klason lignin
$^c$NPA per unit of lignin calculated as ($NP_{lignified}$ − $NP_{nonlignified}$)/Klason lignin
NS, not significant (P = 0.43).

Cell Wall Fermentability:

As in a previous study [72], the biphasic production of fermentation gasses from cell walls during in vitro incubation with mixed rumen microflora were best described with a two-pool logistic model with two discrete lag times. For both experiments, fermentation of both pools in nonlignified cell walls commenced after a lag of <2.5 h, but the primary pool had roughly a 5-fold greater rate and extent of gas production than the secondary pool (Tables 1 and 2). Nonlignified cell walls were extensively degraded, leaving only 21 mg/g of NP. Based on the polysaccharide composition and fermentation characteristics of primary maize walls, it was previously speculated the larger pool represented rapidly fermented non-cellulosic polysaccharides, while the smaller pool represented slowly fermented cellulose [72]. The relative size and fermentation rate of these two pools, is however, strikingly similar to those observed in graminaceous crops [73], which undoubtedly possess a different and more complex structural polysaccharide makeup. This, in contrast to the earlier supposition, suggests the pools do not reflect the fermentation of individual structural polysaccharides.

In both experiments, total gas AB declined 24% and NP increased by ~100 mg/g when cell walls were artificially lignified with normal monolignols (coniferyl and sinapyl alcohols 1, 2) to a Klason lignin content of 150 mg/g (Tables 1 and 2). Lignification with normal monolignols had little effect on lag $L_1$, but rate $k_1$ and gas production A for the large rapidly degraded pool decreased by 57 and 24%, respectively. Conversely for the smaller pool, lignification with normal monolignols dramatically increased lag $L_2$ by 10.7 to 17.5 h and decreased gas production B by 30 to 70%, with comparatively minor effects on rate $k_2$. Previous studies with grass stems and tissues indicated that lignification can increase lag time and reduce the rate and extent of cell wall fermentation [74, 75].

In the first experiment, substituting one-third of normal monolignols with methyl caffeate 5, caffeoylquinic acid 6, or feruloylquinic acid 8 strikingly improved total gas AB and reduced NP for lignified cell walls, primarily through increasing rate $k_1$ and gas production A from the large rapidly digested pool (Table 1). These monolignol substitutes also reduced lag times for both pools, particularly lag $L_2$ of the small slowly digested pool. These monolignol substitutes also lessened fermentation gas reduction (FGR) and nonfermentable polysaccharide accumulation (NPA) per unit of lignin, indicating that factors in addition to reduced lignin content contributed to enhanced fermentability (Table 1). Caffeate, like other benzene-1,2-diols, might internally trap lignin quinone-methide intermediates [5, 76] to limit the cross-linking of lignin to polysaccharides and enhance the enzymatic hydrolysis of cell walls [42]. Incorporation of hydrophilic caffeoyl or quinic acid moieties into lignin might also enhance penetration or limit irreversible binding of hydrolytic enzymes to the lignocellulosic matrix, but identifying actual causative factors requires further study.

While not evident from the kinetics of gas production, reductions in NP and NPA indicated that a modest improvement in fermentability occurred when one-third of normal monolignols were substituted with guaiacylglycerol 4, epigallocatechin 10, or epigallocatechin gallate 11 (Table 1). In contrast, dihydroconiferyl alcohol 3 had no effect, while incorporation of epicatechin 9 and especially methyl ferulate 7 adversely affected cell wall fermentability by decreasing rate $k_1$ and gas production A and AB, and by increasing NP, FGR, and NPA. Among cell walls lignified with catechins, greater 1,2-diol functionality enhanced fermentability, primarily by increasing rate $k_1$ and gas production AB and by decreasing lag $L_2$, NP, FGR, and NPA—again implicating reduced hydrophobicity or cross-linking as playing a role—but underlying mechanisms await revelation. In contrast, increased sidechain hydroxylation of incorporated phenylpropanoids (i.e., dihydroconiferyl alcohol vs. guaiacylglycerol) slightly increased fermentability as indicated by modest reductions (P<0.1) in NP or NPA.

In the second experiment, substituting one-third of a normal monolignol (coniferyl alcohol) with feruloyl esters did not alter cell wall fermentability (Table 2). Among the feruloyl ester treatments, increases in side chain hydroxylation slightly improved fermentability as indicated by an increased rate $k_1$ and a reduced lag $L_2$, NP and NPA. Incorporating 1,4-di-O-diferuloyl threitol 16 and particularly 1,3-di-O-feruloyl glycerol 15 into lignin, however, increased rate $k_1$ and reduced both NP and NPA compared to cell walls lignified solely with coniferyl alcohol. While having relatively modest effects on fermentability of nonpretreated cell walls, incorporation of diferuloyl polyol esters (and other readily cleaved bi-phenolic conjugates like epigallocatechin gallate) could substantially boost pretreatment efficacy for removing lignin prior to biomass saccharification. Other biomimetic model studies by our group recently demonstrated the potential for bi-phenolic conjugates to improve delignification and saccharification [40].

Figure 7:
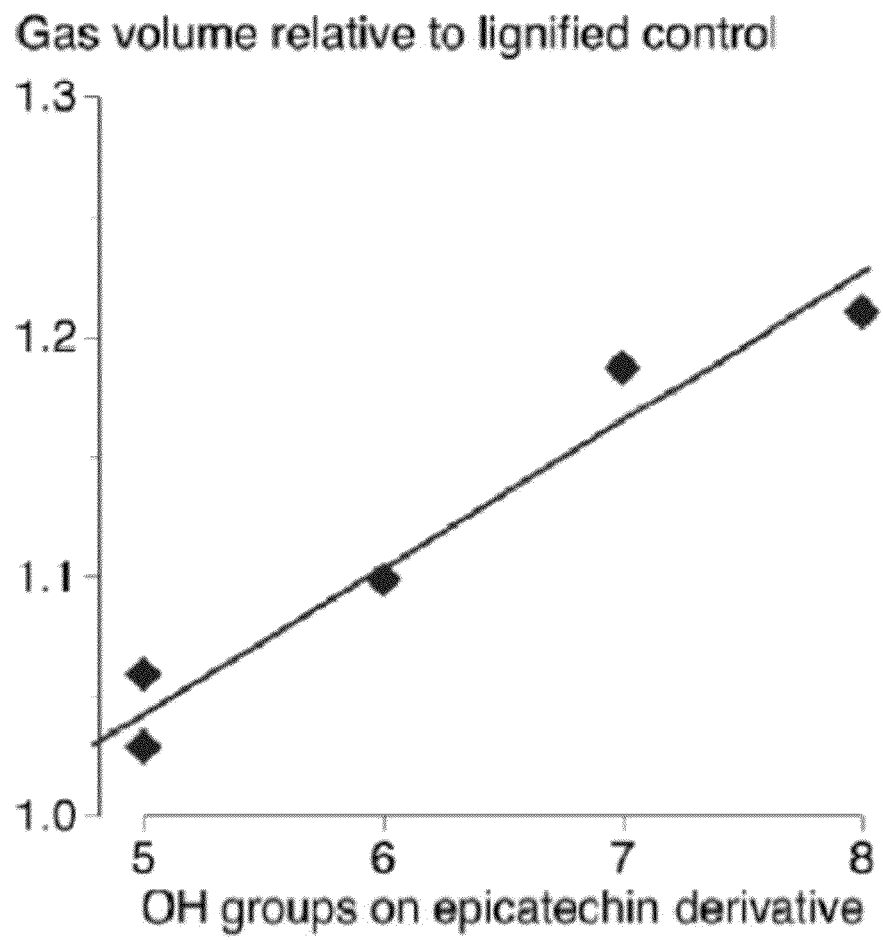
FIG. 7. A graph depicting the relationship of final gas production (fermentability) to the number of OH groups on the catechin derivatives.

In Table 3, catechin derivatives were added with normal monolignols to cell walls (as described herein) to form a quantity of lignin essentially equal to the high lignin control. Epicatechin (EC), epicatechin gallate (ECG) and epigallocatechin gallate (EGCG) readily polymerized with monolignols to form lignin in concentrations equal to the high lignin control. Lignin concentrations were somewhat depressed when epigallocatechin and epicatechin vanillate were used to lignify cell walls. Lignified cell walls were incubated in vitro with rumen microflora, which produce a potent array of cell wall-degrading enzymes. Gas production during incubation of cell walls (positively and highly related to cell wall fermentation and utilization by rumen microflora) was considerably enhanced by most catechin derivatives, especially epicatechin gallate, epigallocatechin gallate, or epigallocatechin. Improved fermentability with these catechin derivatives was further supported by lower levels of nonfermented polysaccharides (NP) remaining after incubation with rumen microflora and by lower gas reduction per unit lignin (GRL) and lower nonfermented polysaccharide accumulation per unit lignin (NPAL) in cell walls. Enhanced fermentability of cell walls was positively related to the degree of catechin hydroxylation. See FIG. 7, which depicts the relationship of final gas production (fermentability) to the number of OH groups on the catechin derivatives.

TABLE 3

Klason lignin and in vitro ruminal fermentability of maize cell walls artificially lignified with a binary mixture of coniferyl alcohol (CA) and sinapyl alcohol (SA) or trinary mixtures of CA and SA with epicatechin (EC), epigallocatechin (EGC), epicatechin gallate (ECG), epigallocatechin gallate, (EGCG), or epicatechin vanillate (ECV).

| Monolignols | Lignin mg/g | Gas production (mL/g) 6 h | 12 h | 48 h | NP[a] (mg/g) | GRL[b] (mL/mg) | NPAL[c] (mg/mg) |
|---|---|---|---|---|---|---|---|
| Nonlignified control | 25.5c[d] | 235a | 318a | 356a | 20e | — | — |
| CA:SA low lignin control | 148.8b | 72c | 177cd | 257c | 174b | 0.80ab | 1.26ab |
| CA:SA high lignin control | 174.7a | 52cd | 129e | 218d | 239a | 0.92a | 1.48a |
| CA:SA:EC | 181.6a | 38d | 88f | 224d | 213a | 0.84ab | 1.24bc |
| CA:SA:EGC | 147.2b | 100b | 232b | 283b | 100d | 0.60c | 0.66e |
| CA:SA:ECG | 178.9a | 65cd | 166d | 259c | 146bc | 0.63c | 0.83de |
| CA:SA:EGCG | 173.4a | 73c | 186c | 264c | 120cd | 0.62c | 0.68e |
| CA:SA:ECV | 153.1b | 68c | 182cd | 272bc | 116cd | 0.66c | 0.76de |

[a]Nonfermented polysaccharides (NP)
[b]Gas reduction per unit lignin (GRL) calculated as [Nonlignified − Lignified gas production at 48 h]/Klason lignin
[c]Nonfermented polysaccharide accumulation per unit lignin (NPAL) calculated as [Lignified − Nonlignified NP at 48 h]/Klason lignin
[d]Means within columns with unlike letters differ (P < 0.05).

In Table 4, cell walls as described in Table 3 and cell wall residues were collected after a weak acid or weak alkaline pretreatment were subjected to enzymatic hydrolysis with a crude fungal cellulase and xylanase mixture. The release of glucose, the main sugar of interest for fermentation into biofuels, was monitored during enzymatic hydrolysis. As noted for Table 3, the inclusion of most catechin derivatives enhances glucose production, especially at the early stages of hydrolysis (6 h) and this was more pronounced after weak acid or base pretreatment of cell walls.

TABLE 4

Klason lignin of cell walls and enzymatic release of glucose from cell walls and from cell wall residues collected after pretreatment with 0.05% solutions of H$_2$SO$_4$ or NaOH at 100° C. for 1 h.

| Monolignols | Klason lignin mg/g | Glucose release (mg/g) Cell walls 6 h | 48 h | H$_2$SO$_4$ residues 6 h | 48 h | NaOH residues 6 h | 48 h |
|---|---|---|---|---|---|---|---|
| Nonlignified control | 25.5c[a] | 590a | 830a | 885a | 972a | 910a | 995a |
| CA:SA low lignin control | 148.8b | 392b | 620bc | 517d | 807d | 646bc | 895bc |
| CA:SA high lignin control | 174.7a | 310c | 530de | 495d | 808d | 581c | 857c |
| CA:SA:EC | 181.6a | 324c | 505e | 544cd | 801d | 698bc | 920bc |
| CA:SA:EGC | 147.2b | 419b | 660b | 680b | 936ab | 787ab | 964ab |
| CA:SA:ECG | 178.9a | 396b | 590cd | 656b | 898bc | 763ab | 946ab |
| CA:SA:EGCG | 173.4a | 358bc | 550de | 629bc | 842cd | 750b | 919bc |
| CA:SA:ECV | 153.1b | 361bc | 548de | 708b | 908b | 675bc | 869c |

Cell walls were artificially lignified with a binary mixture of coniferyl alcohol (CA) and sinapyl alcohol (SA) or trinary mixtures of CA and SA with epicatechin (EC), epigallocatechin (EGC), epicatechin gallate (ECG), epigallocatechin gallate, (EGCG), or epicatechin vanillate (ECV).
[a] Means within columns with unlike letters differ (P < 0.05).

Thus, it is expected that genetic engineering of plants to incorporate catechins, especially epicatechin gallate, epigallocatechin gallate, or epigallocatechin, into lignin will enhance the ruminal fermentability of cell walls for utilization by livestock and the enzymatic hydrolysis of cell walls for the fermentation of sugars into biofuels.

Conclusion

To identify new targets for lignin bioengineering, maize cell walls were artificially lignified via in situ peroxidases with normal monolignols and a variety of phenolic monolignol substitutes normally associated with other plant metabolic pathways. Inclusion of feruloylquinic acid, methyl caffeate, or caffeoylquinic acid with normal monolignols considerably depressed lignin formation and substantially improved cell wall fermentation by rumen microorganisms. In contrast, epicatechin, epigallocatechin, and epigallocatechin gallate readily formed copolymer lignins with monolignols as did the phenylpropanoids dihydroconiferyl alcohol and guaiacylglycerol. Cell wall fermentability was moderately enhanced by catechins with 1,2,3-triol functionality, while inclusion of phenylpropanoids had little or no impact. Mono- or diferuloyl esters with various aliphatic or polyol groups readily formed copolymers with monolignols, but their tendency to accelerate peroxidase inactivation slightly diminished lignin formation in some cases. Relative to cell walls lignified with normal monolignols, copolymerization of mono- or diferuloyl esters into lignin had negative to weakly positive effects on fermentability, which were in part dependent on the quantity of lignin formed and the degree of side group hydroxylation. Overall, monolignol substitutes improved the fermentability of nonpretreated cell walls by depressing lignin formation or possibly by reducing lignin hydrophobicity or cross-linking to structural polysaccharides. Some monolignol substitutes, chiefly readily cleaved bi-phenolic conjugates like epigallocatechin gallate or diferuloyl polyol esters are expected to greatly boost the saccharification of cell walls following chemical pretreatment.

REFERENCES

1. Ralph, J.; Lundquist, K.; Brunow, G.; Lu, F.; Kim, H.; Schatz, P. F.; Marita, J. M.; Hatfield, R. D.; Ralph; S. A.; Christensen, J. H.; Boerjan, W., Lignins: natural polymers from oxidative coupling of 4-hydroxyphenylpropanoids. *Phytochem. Revs.* (2004), 3(1), 29-60.
2. Boerjan, W.; Ralph, J.; Baucher, M., Lignin Biosynthesis. *Annu. Rev. Plant Biol.* (2003), 54, 519-549.
3. Marita, J.; Ralph, J.; Hatfield, R. D.; Chapple, C., NMR characterization of lignins in *Arabidopsis* altered in the activity of ferulate-5-hydroxylase. *Proc. Natl. Acad. Sci.* (1999), 96(22), 12328-12332.
4. Franke, R.; Hemm, M. R.; Denault, J. W.; Ruegger, M. O.; Humphreys, J. M.; Chapple, C., Changes in secondary metabolism and deposition of an unusual lignin in the ref8 mutant of *Arabidopsis*. *Plant J.* (2002), 30(1), 47-59.
5. Ralph, J.; Lapierre, C.; Marita, J.; Kim, H.; Lu, F.; Hatfield, R. D.; Ralph, S. A.; Chapple, C.; Franke, R.; Hemm, M. R.; Van Doorsselaere, J.; Sederoff, R. R.; O'Malley, D. M.; Scott, J. T.; MacKay, J. J.; Yahiaoui, N.; Boudet, A.-M.; Pearl, M.; Pilate, G.; Jouanin, L.; Boerjan, W., Elucidation of new structures in lignins of CAD- and COMT-deficient plants by NMR. *Phytochem.* (2001), 57(6), 993-1003.
6. Ralph, J.; Brunow, G.; Boerjan, W., Lignins. In *Encyclopedia of Life Sciences*, John Wiley & Sons, Ltd.: Chichester, UK, (2007); in press.
7. Ralph, J.; Kim, H.; Lu, F.; Grabber, J. H.; Boerjan, W.; Leplé, J.-C.; Berrio Sierra, J.; Mir Derikvand, M.; Jouanin, L.; Lapierre, C., Identification of the structure and origin of a thioacidolysis marker compound for ferulic acid incorporation into angiosperm lignins (and a pseudo-marker compound for cinnamoyl-CoA reductase deficiency). *Plant J.* (2007), submitted.
8. Ralph, J., What makes a good monolignol substitute? In *The Science and Lore of the Plant Cell Wall Biosynthesis, Structure and Function*, Hayashi, T., Ed. Universal Publishers (BrownWalker Press): Boca Raton, Fla., (2006); pp 285-293.
9. Ralph, J.; Bunzel, M.; Marita, J. M.; Hatfield, R. D.; Lu, F.; Kim, H.; Schatz, P. F.; Grabber, J. H.; Steinhart, H., Peroxidase-dependent cross-linking reactions of p-hydroxycinnamates in plant cell walls. *Phytochem. Revs.* (2004), 3(1), 79-96.
10. Ralph, J.; Kim, H.; Peng, J.; Lu, F., Arylpropane-1,3-diols in lignins from normal and CAD-deficient pines. *Org. Lett.* (1999), 1(2), 323-326.
11. Ralph, J.; MacKay, J. J.; Hatfield, R. D.; O'Malley, D. M.; Whetien, R. W.; Sederoff, R. R., Abnormal lignin in a loblolly pine mutant. *Science* (1997), 277, 235-239.
12. Ward, G.; Hadar, Y.; Dosoretz, C. G., Inactivation of lignin peroxidase during oxidation of the highly reactive substrate ferulic acid. *Enzyme Microb Tech* (2001), 29(1), 34-41.
13. Huang, L. S.; Colas, C.; de Montellano, P. R. O., Oxidation of carboxylic acids by horseradish peroxidase results in prosthetic heme modification and inactivation. *J. Am. Chem. Soc.* (2004), 126(40), 12865-12873.
14. Tobimatsu, Y.; Takano, T.; Kamitakahara, H.; Nakatsubo, F., Studies on the dehydrogenative polymerizations of monolignol beta-glycosides. Part 2: Horseradish peroxidase catalyzed dehydrogenative polymerization of isoconiferin. *Holzforschung* (2006), 60(5), 513-518.
15. Lu, F.; Ralph, J., Preliminary evidence for sinapyl acetate as a lignin monomer in kenaf. *Chem. Commun.* (2002), (1), 90-91.
16. Lu, F.; Ralph, J. Novel β-β-structures in natural lignins incorporating acylated monolignols, *Thirteenth International Symposium on Wood, Fiber, and Pulping Chemistry*, Auckland, New Zealand, (2005); APPITA, Australia: pp 233-237.
17. Grabber, J. H.; Hatfield, R. D.; Ralph, J., Diferulate cross-links impede the enzymatic degradation of nonlignified maize walls. *J. Sci. Food Agr.* (1998), 77(2), 193-200.
18. Stewart, J. J.; Akiyama, T.; Chapple, C. C. S.; Ralph, J.; Mansfield, S. D., Lignins with Extreme Syringyl Levels: The Effects of Over-Expression of Ferulate 5-Hydroxylase on Lignin Structure in Hybrid Poplar. *J. Biol. Chem.* (2007), submitted.
19. Ralph, J.; Helm, R. F.; Quideau, S.; Hatfield, R. D., Lignin-feruloyl ester cross-links in grasses. Part 1. Incorporation of feruloyl esters into coniferyl alcohol dehydrogenation polymers. *J. Chem. Soc., Perkin Trans.* 1 (1992), (21), 2961-2969.
20. Ralph, J.; Hatfield, R. D.; Piquemal, J.; Yahiaoui, N.; Pean, M.; Lapierre, C.; Boudet, A.-M., NMR characterization of altered lignins extracted from tobacco plants downregulated for lignification enzymes cinnamyl-alcohol dehydrogenase and cinnamoyl-CoA reductase. *Proc. Natl. Acad. Sci.* (1998), 95(22), 12803-12808.
21. Ralph, J.; Akiyama, T.; Kim, H.; Lu, F.; Schatz, P. F.; Marita, J. M.; Ralph, S. A.; Reddy, M. S. S.; Chen, F.; Dixon, R. A., Effects of coumarate-3-hydroxylase down-regulation on lignin structure. *J. Biol. Chem.* (2006), 281 (13), 8843-8853.
22. Grabber, J. H.; Ralph, J.; Hatfield, R. D.; Quideau, S.; Kuster, T.; Pell, A. N., Dehydrogenation polymer-cell wall complexes as a model for lignified grass walls. *J. Agr. Food Chem.* (1996), 44(6), 1453-1459.
23. Blee, K. A.; Wheatley, E. R.; Bonham, V. A.; Mitchell, G. P.; Robertson, D.; Slabas, A. R.; Burrell, M. M.; Wojtaszek, P.; Bolwell, G. P., Proteomic analysis reveals a novel set of cell wall proteins in a transformed tobacco cell culture that synthesises secondary walls as determined by biochemical and morphological parameters. *Planta* (2001), 212(3), 404-415.
24. Ohlsson, A. B.; Djerbi, S.; Winzell, A.; Bessueille, L.; Staldal, V.; Li, X. G.; Blomqvist, K.; Bulone, V.; Teeri, T. T.; Berglund, T., Cell suspension cultures of *Populus tremula×P-tremuloides* exhibit a high level of cellulose synthase gene expression that coincides with increased in vitro cellulose synthase activity. *Protoplasma* (2006), 228 (4), 221-229.

25. Wagner, A.; Ralph, J.; Akiyama, T.; Flint, H.; Phillips, L.; Torr, K. M.; Nanayakkara, B.; Te Kiri, L., Modifying lignin in conifers: The role of HCT during tracheary element formation in *Pinus radiata Proc. Natl. Acad. Sci.* (2007), 104(28), 11856-11861.

26. Lapierre, C., Application of new methods for the investigation of lignin structure. In *Forage Cell Wall Structure and Digestibility*, Jung, H. G.; Buxton, D. R.; Hatfield, R. D.; Ralph, J., Eds. ASA-CSSA-SSSA: Madison, Wis., (1993); pp 133-166.

27. Lu, F.; Ralph, J., Derivatization followed by reductive cleavage (DFRC method), a new method for lignin analysis: protocol for analysis of DFRC monomers. *J. Agr. Food Chem.* (1997), 45(7), 2590-2592.

28. Lu, F.; Ralph, J., Non-degradative dissolution and acetylation of ball-milled plant cell walls; high-resolution solution-state NMR. *Plant J.* (2003), 35(4), 535-544.

29. Ralph, J., Dissolution of the entire plant cell wall fraction for solution-state NMR (and chemometrics). In *Fifth Umeå-Imperial Minisymposium on Chemometrics and Metabonomics*, Umeå, Sweden, (2006).

30. Hedenström, M.; Wiklund, S.; Ralph, J.; Edlund, U.; Sundberg, B. A novel approach for analysis of poplar wood using two-dimensional NMR spectroscopy on dissolved whole cell walls in combination with chemometrics *XIth Cell Wall Meeting*, Copenhagen, Denmark, (2007).

31. Pan, X. J.; Arato, C.; Gilkes, N.; Gregg, D.; Mabee, W.; Pye, K.; Xiao, Z. Z.; Zhang, X.; Saddler, J., Biorefining of softwoods using ethanol organosolv pulping: Preliminary evaluation of process streams for manufacture of fuel-grade ethanol and co-products. *Biotechnol. Bioeng.* (2005), 90(4), 473-481.

32. Holtzapple, M. T.; Lundeen, J. E.; Sturgis, R.; Lewis, J. E.; Dale, B. E., Pretreatment of lignocellulosic municipal solid waste by ammonia fiber explosion (AFEX). *Appl. Biochem. Biotechnol* (1992), 0273-2289.

33. Chen, F.; Dixon, R. A., Lignin modification improves fermentable sugar yields for biofuel production. *Nature Biotechnol.* (2007), 25(7), 759-761.

34. Chapple, C.; Ladisch, M.; Meilan, R., Loosening lignin's grip on biofuel production. *Nature Biotechnol.* (2007), 25(7), 746-748.

35. Ralph, J.; Brunow, G.; Harris, P. J.; Dixon, R. A.; Boerjan, W., Lignification: Are lignins biosynthesized via simple combinatorial chemistry or via proteinaceous control and template replication? In *Advances in Polyphenols Research*, Daayf, F.; El Hadrami, A.; Adam, L.; Ballance, G. M., Eds. Blackwell Publishing: Oxford, UK, (2007); in press.

36. Lu F, Ralph J: Novel tetrahydrofuran structures derived from β-β-coupling reactions involving sinapyl acetate in kenaf lignins. *Org Biomol Chem* 2008, 6:3681-3694.

37. Grabber J H, Ralph J, Hatfield R D: Cross-Linking of maize walls by ferulate dimerization and incorporation into lignin. *J Agric Food Chem* 2000, 48:6106-6113.

38. Grabber J H, Ralph J, Hatfield R D: Model studies of ferulate-coniferyl alcohol cross-product formation in primary maize walls: Implications for lignification in grasses. *J Agric Food Chem* 2002, 50:6008-6016.

39. Vanholme R, Morreel K, Ralph J, Boerjan W: Lignin engineering. *Curr Opin Plant Biol* 2008, 11:1-8.

40. Grabber J H, Hatfield R D, Lu F, Ralph J: Coniferyl ferulate incorporation into lignin enhances the alkaline delignification and enzymatic degradation of cell walls. *Biomacromolecules* 2008, 9:2510-2516.

41. Grabber J H, Hatfield R D: Methyl esterification divergently affects the degradability of pectic uronosyls in non-lignified and lignified maize cell walls. *J Ag Food Chem* 2005, 53:1546-1549.

42. Grabber J H, Hatfield R D, Ralph J: Apoplastic pH and monolignol addition rate effects on lignin formation and cell wall degradability in maize. *J Ag Food Chem* 2003, 51:4984-4989.

43. Grabber J H: How do lignin composition, structure, and cross-linking affect degradability? A review of cell wall model studies. *Crop Sci* 2005, 45:820-831.

44. Doane P H, Schofield P, Pell A N: Neutral detergent fiber disappearance and gas and volatile fatty acid production during the in vitro fermentation of six forages. *J Anim Sci* 1997, 75:3342-3352.

45. Getachew G, Blummel M, Makkar H P S, Becker K: In vitro gas measuring techniques for assessment of nutritional quality of feeds: a review. *Anim Feed Sci Technol* 1998, 72:261-281.

46. Weimer P J, Dien B S, Springer T L, Vogel K P: In vitro gas production as a surrogate measure of the fermentability of cellulosic biomass to ethanol. *Appl Microbiol Biotechnol* 2005, 67:52-58.

47. Quideau S, Ralph J: Facile large-scale synthesis of coniferyl, sinapyl, and p-coumaryl alcohol. *J Agric Food Chem* 1992, 40:1108-1110.

48. Kim H, Ralph J: Simplified preparation of coniferyl and sinapyl alcohols. *J Ag Food Chem* 2005, 55:3693-3695.

49. Hemmerle H, Burger H J, Below P, Schubert G, Rippel R, Schindler P W, Paulus E, Herling A W: Chlorogenic acid and synthetic chlorogenic acid derivatives: Novel inhibitors of hepatic glucose-6-phosphate translocase. *J Med Chem* 1997, 40:137-145.

50. Ulibarri G, Nadler W, Skrydstrup T, Audrain H, Chiaroni A, Riche C, Grierson D S: Construction of the bicyclic core structure of the enediyne antibiotic Esperamicin-a(1) in either enantiomeric form from (−)-quinic acid. *J Org Chem* 1995, 60:2753-2761.

51. Lu F, Ralph J: Facile synthesis of 4-hydroxycinnamyl p-coumarates. *J Agric Food Chem* 1998, 46:2911-2913.

52. Grabber J H, Lu F: Formation of syringyl-rich lignins in maize as influenced by feruloylated xylans and p-coumaroylated monolignols. *Planta* 2007, 226:741-751.

53. Hatfield R D, Jung H G, Ralph J, Buxton D R, Weimer P J: A comparison of the insoluble residues produced by the Klason lignin and acid detergent lignin procedures. *J Sci Food Agric* 1994, 65:51-58.

54. Kim H, Ralph J: Solution-state 2D NMR of ball-milled plant cell wall gels in DMSO-d6/pyridine-d5. *Org Biomol Chem* 2010, 8: 576-591.

55. Weimer P J, Mertens D R, Ponnampalam E, Severin B F, Dale B E: FIBEX-treated rice straw as a feed ingredient for lactating dairy cows. *Anim Feed Sci Technol* 2003, 103:41-50.

56. Dubois M, Giles K A, Hamilton J K, Rebers P A, Smith F: Colorimetric method for determination of sugars and related substances. *Anal Chem* 1956, 28:350-356.

57. Steel R G D, Torrie J H: Principles and procedures of statistics, 2nd edition. New York: McGraw-Hill Publishing Co.; 1980.

58. SAS: SAS PC Windows Version 9.1.3. In. Cary, N.C., USA: SAS Institute Inc.; 2003.

59. Ferrer M A, Barcelo A R: Inactivation of cell wall acidic peroxidase isoenzymes during the oxidation of coniferyl alcohol in Lupinus. *Phytochemistry* 1994, 36:1161-1163.

60. Huang Q, Huang Q, Pinto R A, Griebenow K, Schweitzer-Stenner R, Weber Jr W J: Inactivation of horseradish peroxidase by phenoxyl radical attack. *J Am Chem Soc* 2005, 127:1431-1437.
61. Evans J J, Himmelsbach D S: Incorporation of peroxidase into synthetic lignin. *J Agric Food Chem* 1991, 39:830-832.
62. Hatfield R D, Ralph J, Grabber J H: A potential role for sinapyl p-coumarate as a radical transfer mechanism in grass lignin formation. *Planta* 2008, 228:919-928.
63. Clifford M N: Chlorogenic acids and other cinnamates—nature, occurrence and dietary burden. *J Sci Food Agric* 1999, 79:362-372.
64. Arrieta-Baez D, Stark R E: Modeling suberization with peroxidase-catalyzed polymerization of hydroxycinnamic acids: Cross-coupling and dimerization reactions. *Phytochemistry* 2006, 67:743-753.
65. Russell W R, Burkitt M J, Scobbie L, Chesson A: Radical formation and coupling of hydroxycinnamic acids containing 1,2-dihydroxy substituents. *Bioorganic Chem* 2003, 31:206-215.
66. Guyot S, Vercauteren J, Cheynier V: Structural determination of colourless and yellow dimers resulting from (+)-catechin coupling catalysed by grape polyphenoloxidase. *Phytochemistry* 1996, 42:1279-1288.
67. Hosny M, Rosazza J P N: Novel oxidations of (+)-catechin by horseradish peroxidase and laccase. *J Ag Food Chem* 2002, 50:5539-5545.
68. Kusano R, Tanaka T, Matsuo Y, Kouno I: Structures of epicatechin gallate trimer and tetramer produced by enzymatic oxidation. *Chem Pharm Bull* 2007, 55:1768-1772.
69. Grabber J H, Hatfield R D, Ralph J, Zon J, Amrhein N: Ferulate cross-linking in cell walls isolated from maize cell suspensions. Phytochemistry 1995, 40:1077-1082.
70. Oosterveld A, Grabber J H, Beldman G, Ralph J, Voragen A G J: Formation of ferulic acid dehydrodimers through oxidative cross-linking of sugar beet pectin. *Carbohydr Res* 1997, 300:179-181.
71. Bunzel M, Ralph J, Funk C, Steinhart H: Isolation and identification of a ferulic acid dehydrotrimer from saponified maize bran insoluble fiber. *Eur Food Res Technol* 2003, 217:128-133.
72. Grabber J H, Mertens D R, Kim H, Funk C, Lu F, Ralph J: Cell wall fermentation kinetics are impacted more by lignin content and ferulate cross-linking than by lignin composition. *J Sci Food Agric* 2009, 89:122-129.
73. Van Soest P J, Van Amburgh M E, Robertson J B, Knaus W F: Validation of the 2.4 times lignin factor for ultimate extent of NDF digestion, and curve peeling rate of fermentation curves into pools. In: *Cornell Nutrition Conference for Feed Manufacturers; Syracuse, N.Y.*: Cornell University, Ithaca, N.Y.; 2005: 139-149.
74. Lopez S, Murison S D, Travis A J, Chesson A: Degradability of parenchyma and sclerenchyma cell walls isolated at different developmental stages from a newly extended maize internode. *Acta Bot Neerl* 1993, 42:165-174.
75. Buxton D R, Brasche M R: Digestibility of structural carbohydrates in cool-season grass and legume forages. *Crop Science* 1991, 31:1338-1345.
76. Ralph J, Schatz P F, Lu F, Kim H, Akiyama T, Nelsen S F: Quinone methides in lignification. In: *Quinone Methides*. Edited by Rokita S. Hoboken, N.J.: Wiley-Blackwell; 2009.
77. Kim H, Ralph J, Akiyama T: Solution-state 2D NMR of ball-milled plant cell wall gels in DMSO-d6. *Bioenerg Res* 2008, 1:56-66.
78. Zhu N, Huang T C, Yu Y, LaVoie E J, Yang C S, Ho C T: Identification of oxidation products of (−)-epigallocatechin gallate and (−)-epigallocatechin with $H_2O_2$. *J Ag Food Chem* 2000, 48:979-981.
79. Zhu N, Wang M, Wei G J, Lin J K, Yang C S, Ho C T: Identification of reaction products of (−)-epigallochatechin, (−)-epigallochatechin gallate and pyrogallol with 2,2-diphenyl-1-picrylhydrazyl radical. *Food Chem* 2001, 73:345-349.
80. Ralph S A, Landucci L L, Ralph J: NMR Database of Lignin and Cell Wall Model Compounds. Available over Internet at http://ars.usda.gov/Services/docs.htm-?docid=10429, updated at least annually since 1993. 2005.

What is claimed is:

1. A method of manufacturing modified lignin, the method comprising conducting a lignin-producing polymerization reaction in the presence of one or more polymerizable monomers selected from the group consisting of:

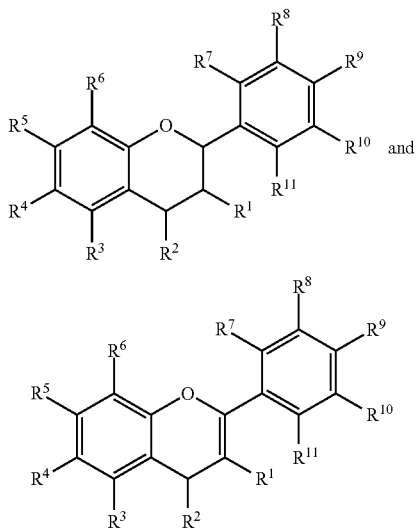

wherein $R^1$ and $R^2$ are independently selected from the group consisting of hydrogen, =O, hydroxy, alkyloxy, alkanoyl, alkanoyloxy, hydroxy-substituted alkoxy or alkanoyl or alkanoyloxy, benzoyloxy, monosaccharide, disaccharide, gallate esters of mono- and disaccharides, and mono-, di- and tri-hydroxy-substituted benzoyloxy;

$R^3$-$R^6$ are independently selected from the group consisting of hydrogen, hydroxy, alkyl, alkyloxy, hydroxy-substituted alkyl, hydroxy-substituted alkoxy, benzoyloxy, and mono-, di- and tri-hydroxy-substituted benzoyloxy, provided that at least one of $R^3$-$R^6$ is hydroxy;

$R^7$-$R^{11}$ are independently selected from the group consisting of hydrogen, hydroxy, alkyl, alkyloxy, hydroxy-substituted alkyl, and hydroxy-substituted alkoxy, provided that at least one of $R^7$-$R^{11}$ is hydroxyl;

wherein at least one of the polymerizable monomers is incorporated into the resulting lignin.

2. The method of claim 1, comprising conducting the polymerization reaction in the presence of a polymerizable monomer wherein $R^2$ is hydrogen, and $R^1$ is:

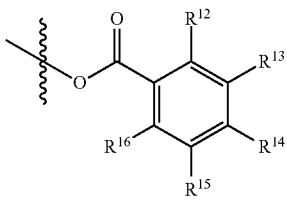

wherein $R^{12}$-$R^{16}$ are independently selected from the group consisting of hydrogen, hydroxy, alkyloxy, alkanoyl, alkanoyloxy, hydroxy-substituted alkoxy or alkanoyl or alkanoyloxy, provided that $R^{12}$-$R^{16}$ are not simultaneously hydrogen.

3. The method of claim 1, comprising conducting the polymerization reaction in the presence of a polymerizable monomer selected from the group consisting of:

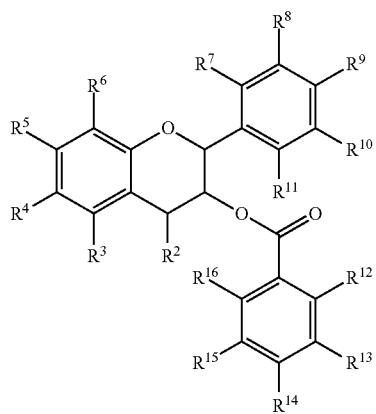

wherein $R^2$-$R^{11}$ are as defined in claim 1, and $R^{12}$-$R^{16}$ are independently selected from the group consisting of hydrogen and hydroxy, provided that $R^{12}$-$R^{16}$ are not simultaneously hydrogen.

4. The method of claim 3, wherein at least one of $R^{13}$, $R^{14}$, or $R^{15}$ is hydroxy.

5. The method of claim 3, wherein at least two of $R^{13}$, $R^{14}$, or $R^{15}$ are hydroxy.

6. The method of claim 3, wherein $R^{13}$, $R^{14}$, and $R^{15}$ are hydroxy.

7. The method of claim 1, comprising conducting the polymerization reaction in the presence of a polymerizable monomer selected from the group consisting of catechin, epicatechin, gallocatechin, epigallocatechin, gallocatechin gallate, epigallocatechin gallate, and optical isomers thereof.

8. The method of claim 1, wherein $R^1$, $R^3$, and $R^5$ are hydroxy.

9. The method of claim 1, wherein at least one of $R^8$, $R^9$, or $R^{10}$ is hydroxy.

10. The method of claim 1, wherein at least two of $R^8$, $R^9$, or $R^{10}$ are hydroxy.

11. The method of claim 1, wherein $R^8$, $R^9$, or $R^{10}$ are hydroxy.

12. The method of any one of the proceeding claims, comprising conducting the polymerization reaction in the presence of at least one polymerizable monomer selected from the group consisting of coniferyl alcohol, dihydroconiferyl alcohol, and sinapyl alcohol.

13. The method of any one of claims 1 to 11, comprising conducting the polymerization reaction in the absence of at least one polymerizable monomer selected from the group consisting of coniferyl alcohol, dihydroconiferyl alcohol, and sinapyl alcohol.

14. The method of claim 1, wherein from about 10% by wt to about 60% by wt of the polymerizable monomers are reacted in the polymerization reaction.

15. The method of claim 1, wherein the polymerization reaction is conducted in vitro.

16. The method of claim 1, wherein the polymerization reaction is conducted in vivo.

17. A modified lignin produced by a method as recited in claim 1.

18. The method of claim 1, comprising conducting the polymerization reaction in the presence of at least one polymerizable monomer selected from the group consisting of coniferyl alcohol, p-coumaryl alcohol, and sinapyl alcohol.

19. The method of claim 1, comprising conducting the polymerization reaction in the absence of at least one polymerizable monomer selected from the group consisting of coniferyl alcohol, p-coumaryl alcohol, and sinapyl alcohol.

* * * * *